United States Patent [19]
Leigh et al.

[11] Patent Number: 6,020,337
[45] Date of Patent: *Feb. 1, 2000

[54] ELECTRONEGATIVE-SUBSTITUTED LONG CHAIN XANTHINE COMPOUNDS

[75] Inventors: Alistair J. Leigh, Brier; John Michnick; Anil M. Kumar, both of Seattle; J. Peter Klein, Vashon, all of Wash.; Gail Underiner, Malvern, Pa.

[73] Assignee: Cell Therapeutics, Inc., Seattle, Wash.

[ * ] Notice: This patent is subject to a terminal disclaimer.

[21] Appl. No.: 08/950,810

[22] Filed: Sep. 16, 1997

Related U.S. Application Data

[63] Continuation-in-part of application No. 08/042,946, Apr. 5, 1993, Pat. No. 5,670,506, and a continuation-in-part of application No. 08/910,579, Jul. 26, 1997.

[51] Int. Cl.$^7$ .......................... A61K 31/52; C07D 473/00
[52] U.S. Cl. .......................... 514/258; 514/263; 544/267; 544/272; 544/277
[58] Field of Search .......................... 514/258; 544/267, 544/272, 277

[56] References Cited

U.S. PATENT DOCUMENTS

| | | | |
|---|---|---|---|
| 3,422,107 | 1/1969 | Mohler et al. | 260/256 |
| 3,737,433 | 3/1987 | Mohler et al. | 260/256 |
| 4,289,776 | 9/1981 | Mohler et al. | 424/253 |
| 4,515,795 | 5/1985 | Hinze et al. | 514/263 |
| 4,576,947 | 3/1986 | Hinze et al. | 514/263 |
| 4,636,507 | 1/1987 | Kreutzer et al. | 514/263 |
| 4,766,142 | 8/1988 | Arcomone et al. | 514/422 |
| 4,833,146 | 5/1989 | Gerbert et al. | 514/263 |
| 4,952,679 | 8/1990 | Hoegerle et al. | 534/618 |
| 4,965,271 | 10/1990 | Mandell et al. | 514/263 |
| 5,039,666 | 8/1991 | Novick et al. | 514/37 |
| 5,086,056 | 2/1992 | Janssens et al. | 514/253 |
| 5,096,906 | 3/1992 | Mandell et al. | 514/263 |
| 5,126,349 | 6/1992 | Deford et al. | 514/269 |
| 5,298,508 | 3/1994 | Jacobson et al. | 514/263 |
| 5,521,315 | 5/1996 | Underiner et al. | 546/243 |
| 5,670,506 | 9/1997 | Leigh et al. | 514/258 |

OTHER PUBLICATIONS

Kanehira et al., Chemicals Abstracts 110: 212848x, p. 757, 1989.
Salikhov et al., Chemical Abstracts 112: 157941m, 1990.
Kanehira et al., Chemical Abstracts 110:212848x p. 757, 1989.
Salikhov et al., Chemical Abstracts 112: 157941m. 1990.
Bianco et al., Blood, 76: Supplement 1 (522), p. 133a "Pentoxifylline (PTX) and GM–CSF Decrease Tumor Necrosis Factor–ALPHA (TNF–α) Levels in Patients Undergoing Allogeneic Bone Marrow Transplantation (BMT)", 1991.
Bryce et al., Arzneim–Forsch./Drug Res., 39:4, pp. 512–517. "Metabolism and Pharmacokinetics of $^{14}$ C–Pentoxifylline in Healthy volunteers", 1989.
Davis et al., Applied Environment Microbial., 48:2, pp. 327–331, "Microbial Models of Mammalian Metobolism: Microbial Reductiona nd Oxidation of Pentoxifylline", Aug. 1984.
Sahkhov et al., Abstract 112:157941m, 1990.
Akhrem et al., Khimigetero Soedin (1979) 2, pp. 230–234.

*Primary Examiner*—Mukund J. Shah
*Assistant Examiner*—Pavanaram K Sripada
*Attorney, Agent, or Firm*—Foley & Lardner

[57] ABSTRACT

Therapeutic compounds, including resolved enantiomers and/or diastereomers, hydrates, salts, solvates and mixtures thereof, having a formula:

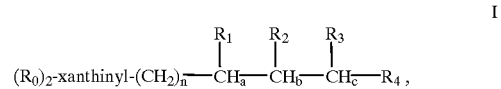

wherein $R_0$ is selected from the group consisting of hydrogen, halo, hydroxyl, amino, substituted or unsubstituted $C_{(1-10)}$ alkyl, $C_{(2-10)}$ alkenyl, cyclic or heterocyclic groups, wherein the substituents of substituted $C_{(1-10)}$ alkyl, $C_{(2-10)}$ alkenyl are other than halo; n is an integer from one to sixteen; $R_1$, $R_2$, and $R_3$ are independently selected from the group consisting of a halo; haloacetoxy; hydrogen; hydroxy; oxo; —N=C=S; —N=C=O; —O—C≡N; —C≡N; —N=N=N; and —C—$(R_5)_3$, $R_5$ being independently a halo or hydrogen, at least one $R_5$ being halo, at least one of $R_1$, $R_2$, and $R_3$ being halo, cyano, isocyano, isothiocyano, azide or haloacetoxy group; $R_4$ is hydrogen, $C_{(1-6)}$ alkyl, $C_{(1-6)}$ alkenyl, cyclo $C_{(4-6)}$ alkyl, or phenyl; one or more hydrogen atoms of $(CH_2)_n$—$CH_a$—$CH_b$—$CH_c$ may be replaced with: i) at least one of halogen atom, hydroxyl, oxo, substituted or unsubstituted $C_{(1-10)}$ alkyl, $C_{(1-10)}$ alkoxyalkyl, or $C_{(2-10)}$ alkenyl; or ii) one or more unsaturated bonds; and any two adjacent carbon atoms of $(CH_2)_n$—$CH_a$—$CH_b$—$CH_c$ may be instead separated by at least one oxygen atom. These compounds are useful in treating or preventing diseases by inhibiting selective second messenger pathways.

17 Claims, 16 Drawing Sheets

ELECTRONEGATIVE-SUBSTITUTED LONG CHAIN XANTHINE COMPOUNDS

This is a Continuation-in-Part Application of U.S. applications Ser. No. 08/042,946, now U.S. Pat. No. 5,670,506, and Ser. No. 08/910,579, filed Apr. 5, 1993 and Jul. 26, 1997, respectively.

The invention provides for a class of substituted xanthinyl compounds that are effective agents to inhibit specific cellular signaling events often induced by noxious or inflammatory stimuli. More specifically, the inventive compounds have at least one of a halogen-, haloacetoxy-, azide-, cyanate-, isocyanate-, isothiocyanate- or nitrile-containing substituent bonded to a xanthinyl.

BACKGROUND OF THE INVENTION

Pentoxifylline [1-(5-oxohexyl)-3,7-dimethylxanthine], abbreviated PTX, is a xanthine derivative widely used medically for increasing blood flow. U.S. Pat. Nos. 3,422,107 and 3,737,433, both to Mohler et al., disclose PTX. Metabolites of PTX were summarized in Davis et al., "Microbial Models of Mammalian Metabolism: Microbial Reduction and oxidation of Pentoxifylline," *Applied and Environmental Microbiology*, Vol. 48, No. 2, pages 327–381, August 1984, and Bryce et al., "Metabolism and Pharmacokinetics of $^{14}$C-Pentoxifylline Healthy Volunteers," *Arzneim-Forsch./Drug Res.* Vol. 39, No. 4, pages 512–517, 1989. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947 to Hinze et al. Other metabolites include 1-(5-pentoyl)-3,7-dimethylxanthine carboxylic acid, designated M4, and 1-(4-butyl)-3,7-dimethylxanthine carboxylic acid, designated M5. In addition, U.S. Pat. Nos. 4,833,146 and 5,039,666 to Gebert et al. and Novick, respectively, disclose use of tertiary alcohol analogs of xanthine for enhancing cerebral blood flow.

PTX and its known metabolites thereof have been shown to have in vivo activity in specific biologic systems. U.S. Pat. No. 4,636,507 to Kreutzer et al. describes an ability of PTX and M1 to enhance chemotaxis in polymorphonuclear leukocytes responding to chemotaxis stimulation. In addition, PTX and related tertiary alcohol substituted xanthines inhibit activity of certain cytokines to affect chemotaxis as described in U.S. Pat. Nos. 4,965,271 and 5,096,906 to Mandell et al. Furthermore, by co-administrating PTX and GM-CSF, patients undergoing allogeneic bone marrow transplant exhibited decreased levels of tumor necrosis factor, TNF. Bianco et al., "Pentoxifylline (PTX) and GM-CSF Decrease Tumor Necrosis Factor (TNF-α) Levels in patients undergoing allogeneic Bone Marrow Transplantation (BMT)," *Blood*, Vol. 76, No. 1, Suppl. 1 (522), page 133a, 1990. Reduction in assayable levels of TNF was accompanied by reduced BMT-related complications. However, in normal volunteers, TNF levels were higher among PTX recipients. Therefore, elevated levels of TNF are not the primary cause of such complications.

These and similar studies have created much interest in xanthinyl-related compounds. For example, Salikhov et al. have produced compounds containing two or three haloalkyl chains. Chemical Abstracts 112: 157941m, 1990. However, no specific utility was ascribed to these compounds.

Further research in our laboratories with PTX, its metabolites, and their activity relating to various biologic systems spurred investigations with potential therapeutic agents heretofore unknown. These agents were identified as potentially therapeutic for treating or preventing disease by inhibiting secondary cellular response to an external or in situ primary stimuli. These investigations sought efficacious therapeutic compounds which would be safe and effective for human or animal administration and would maintain cellular homeostasis in the presence of a variety of deleterious stimuli.

Many diseases are difficult to treat because they have complex mechanisms of action, and multiple, adverse effects on a subject. As an example, cancer has been difficult to treat for this and other reasons. Precise causes of cancer remain unknown. Malignant tumor growth results from many physiologic factors. Cancer cells metastasize (i.e., break through blood vessels and travel to distant body sites) and secrete enzymes called metalloproteases, which "break down" blood vessel walls (proteolysis), allowing the cancer cells to enter the bloodstream and form remote tumors. In addition, tumor cell adhesion receptors (integrins) affect attachment—necessary for tumor residence in organs—of tumor cells to blood vessel walls and normal organs. Cancer cells also secrete certain proteins, such as bFGF, that stimulate new blood vessel development (angiogenesis), these new blood vessels supplying nutrients to promote malignant tumor growth.

Conventional antineoplastic therapies, such as, for example, antimetabolites, alkylating agents and antitumor agents (which target or interfere with DNA and/or synthesis of DNA or its precursors), and biologic therapies (including selective interferons, interleukins and other factors) have significant adverse side effects in patients, not limited to acute toxicity due to effects on rapid-proliferating tissues, such as bone marrow and oral epithelium, myelosuppression and mucositis, renal failure and neurological, hepatic or pulmonary toxicity. Thus, for example, a cancer therapy which effectively prevented, reduced or eliminated malignant tumors without causing deleterious side effects would provide previously unknown treatment.

Compounds disclosed herein and discovered in search of potential disease treatments which would prevent or treat a disease with minimal or no adverse side effects, have biologic activity in representative assays, indicating potential commercial therapy in treating a broad spectrum of clinical indications acting via a variety of disease mechanisms. However, all these mechanisms appear to affect intracellular levels of phosphatidic acids and phosphatidic acid-derived diacylglycerols which occur in response to cellular proliferative stimuli and act as second messengers in a second messenger pathway. Results of this research are the subject matter of this disclosure.

SUMMARY OF THE INVENTION

The invention provides a halogen-, haloacetoxy-, azide-, cyanate-, isocyanate-, isothiocyanate- or nitrile-substituted compounds and pharmaceutical compositions and uses thereof. The inventive compounds are useful in a large variety of therapeutic indications for treating or preventing disease. In particular, the inventive compounds and pharmaceutical compositions thereof provide therapy for diseases caused or advanced by intracellular signaling through specific intracellular signaling pathways, specifically the pathways discussed herein, by inhibiting pathway signaling. Abnormally-induced intracellular signaling is characteristic of diseases treatable using the inventive compounds.

The inventive compounds have the formula:

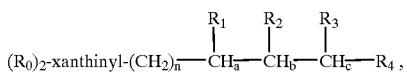

$$(R_0)_2\text{-xanthinyl-}(CH_2)_n-CH_a-CH_b-CH_c-R_4, \quad I$$

wherein $R_0$ is selected from the group consisting of hydrogen, halo, hydroxyl, amino, substituted or unsubstituted $C_{(1-10)}$ alkyl, $C_{(2-10)}$ alkenyl, cyclic or heterocyclic groups, wherein the substituents of substituted $C_{(1-10)}$ alkyl, $C_{(2-10)}$ alkenyl are other than halo; n is an integer from one to sixteen; $R_1$, $R_2$, and $R_3$ are independently selected from the group consisting of halo; haloacetoxy; hydrogen; hydroxy; oxo; —N=C=S; —N=C=O; —O—C≡N; —C≡N; —N=N=N; and —C—$(R_5)_3$, $R_5$ being independently a halo or hydrogen, at least one $R_5$ being halo, at least one of $R_1$, $R_2$, and $R_3$ being a halo, cyano, isocyano, isothiocyano, azide or haloacetoxy group; $R_4$ is hydrogen, $C_{(1-6)}$ alkyl, $C_{(1-6)}$ alkenyl, cyclo $C_{(4-6)}$ alkyl, or phenyl. Alternatively, one or more hydrogen atoms of $(CH_2)_n$—$CH_a$—$CH_b$—$CH_c$ may be substituted, and any two adjacent carbon atoms of $(CH_2)_n$—$CH_a$—$CH_b$—$CH_c$ may be instead separated by at least one oxygen atom. These compounds are useful in treating or preventing diseases by inhibiting selective second messenger pathways.

In some preferred compounds, $R_2$ and $R_3$ are selected from the group consisting of halo, oxo, and hydroxyl group.

DETAILED DESCRIPTION OF THE INVENTION

Figure 1:
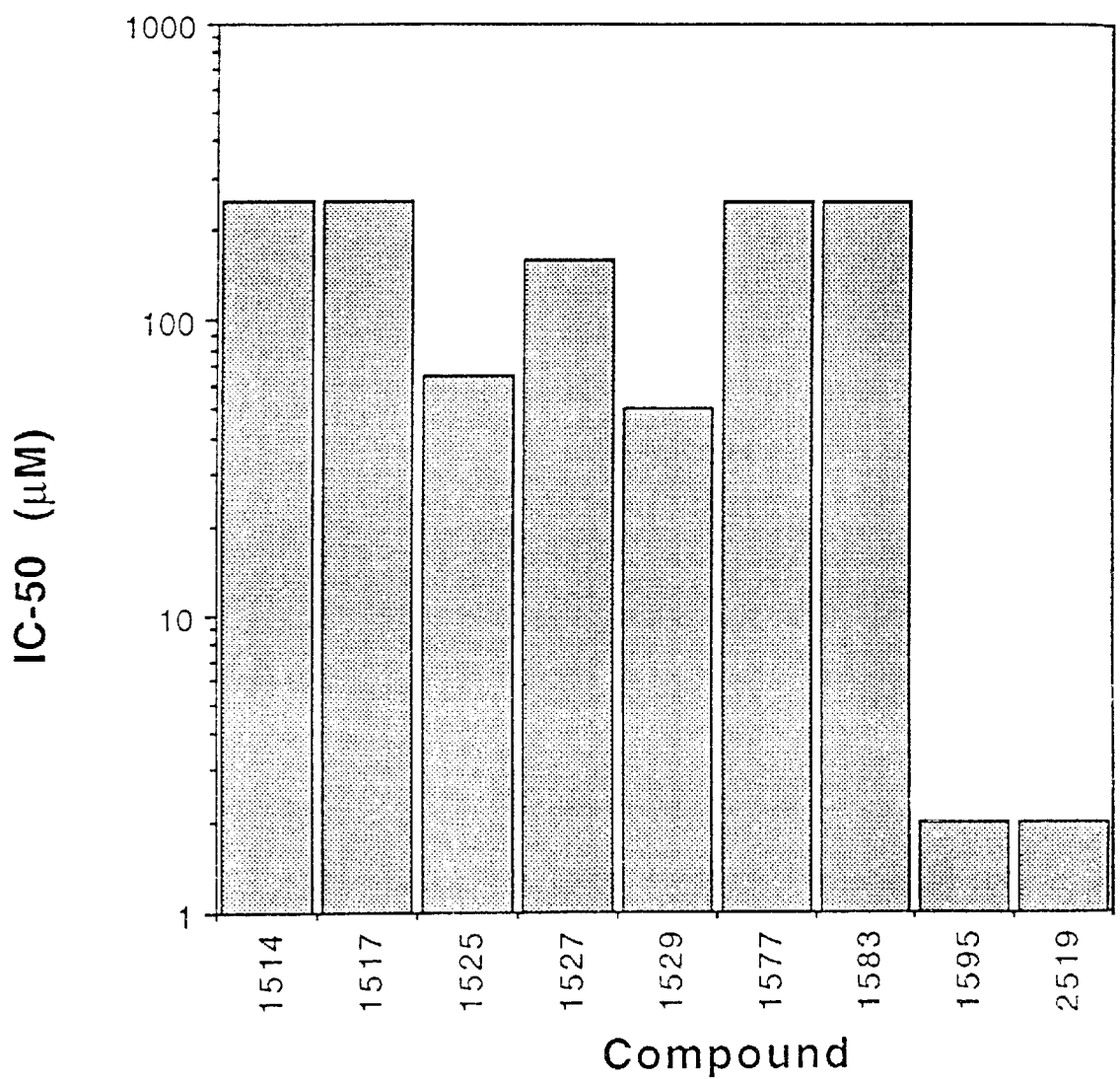
FIG. 1 shows a bar graph of $IC_{50}$ values for five inventive compounds (chemical names and structures below) in a mixed lymphocyte assay to measure immune suppression activity.

The inventive compounds may control cell behavior by a particular phase of a second messenger pathway system (Bursten et al., "Interleukin-1 Rapidly Stimulates Lysophosphatidate Acyltransferase and Phosphatidate Phosphohydrolase Activities in Human Mesangial Cells," *J. Biol. Chem.*, Vol. 266, No. 31, pages 20732–20743, Nov. 5, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
$PLA_2$=phospholipase $A_2$
PLD=phospholipase D
PAA=phosphoarachidonic acid
PC=phosphatidyl choline "remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl- side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. The inventive compounds reduce or eliminate elevated PA and DAG.

These compounds and pharmaceutical compositions of the invention inhibit subspecies of LPAAT and PAPH enzymes with substrate specificity for intermediates with 1,2-diunsaturated and 1-alkyl, 2-unsaturated subspecies. PTX also blocks PAPH in a specific activation pathway that does not involve PI but rather derives from a PA that is largely composed of 1,2-diunsaturated and 1-alkyl, 2-unsaturated subspecies. This was shown, for example, by the demonstration that TNF-stimulated human mesangial cells produce DAG from PI and regenerate PI with or without PTX present. In the latter system there is no evidence to suggest that PA or DAG are derived from sources other than PI. In contrast, the inventive compounds affect that subset of PAPH and LPAAT relating to substrates with unsaturated fatty acids other than arachidonate in the sn-2 position, not the housekeeping forms of these enzymes that serve the PI pathway.

The second messenger pathway of most significance in the invention involves substrates with unsaturated fatty acids in the sn-2 position other than arachidonate and those subspecies of PAPH and LPAAT that are not involved in normal cellular housekeeping functions, which are part of a classical PI pathway. The PAPH and LPAAT enzymes involved in this specific second messenger pathway are stereo-specific for different acyl side chains and substrate isomers. Therefore, the inventive compounds may preferably be substantially enantiomerically pure.

IL-1 activates (through the Type I IL-1 receptor) a lyso-PA acyltransferase (LPAAT) and phosphatidate phosphohydrolase (PAPH) within 5 seconds of cell (for example, human mesangial cells, HMC) exposure. Activation of both enzymes results in production of PA species with sn-1 and sn-2 unsaturated acyl groups, with the majority of sn-2 acyl chains being polyunsaturated. Both IL-1 and a product of LPAAT (1,2-sn-dilinoleoyl PA) activate a signaling pathway involving hydrolysis of PE to PA. This reaction is followed by dephosphorylation of PA to produce both 1,2-sn-diacylglycerol and 1-o-alkyl, or 1-o-alkenyl, acylglycerol (AAG) species. The inventive compounds exert their activity by inhibiting one or both enzymes at an inner leaflet of the plasma membrane. Therefore, appropriate in vitro models for drug activity may measure inhibition of stimulation caused by a proinflammatory cytokine or other inflammatory cellular signal.

Generation of sn-2 unsaturated PA fraction by LPAAT serves to activate G-proteins or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is less than about 0.1% of total membrane lipid mass, is sufficient to activate PLD activity. This quantity of PA is similar to that endogeneously synthesized by LPAAT. The PA-stimulated PLD acts upon PE and should localize to the inner leaflet of the cell membrane, enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 minutes) is maintained by PC-derived PA generated by PC-directed PLD.

Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG upon stimulation with mitogens, although the sources of DAG differ between experimental systems. In nontransformed renal mesangial cells, IL-1β stimulation increased $PLA_2$ and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. A particular species of serum-stimulated DAG is dioleoyl and species of PA are dilinoleoyl and dioleoyl. This upregulation occurs over 4–12 hours and pretreatment of cells with an inventive compound blocks generation of these phospholipid second messengers. The inhibition occurs either through suppressing PA generation de novo from lysoPA, or through inhibition of one or both arms of the Lands cycle. A corresponding lysoPA increase with diminished PA/DAG production suggests inhibition of transacylation of a precursor lipid. Therefore, the ras transformation mediates an upregulation of PA through indirect stimulation of $PLA_2$ and/or LPAAT activity. The inventive compounds inhibit conversion of upregulated lysoPA to PA and subsequently block phenotypic changes induced by PA/DAG in the membrane.

Therapeutic Uses of the Inventive Compounds

Inhibition of second messenger pathway activation, as described above, represents that the inventive compounds are useful in treating a wide variety of clinical indications mediated at the cellular level by a common mechanism. Moreover, in vitro data presented herein provides predictive evidence that a wide variety of clinical indications, having similar effects on the selective second messenger pathway, may be treated by the inventive compounds. These compounds specifically inhibit the second messenger signaling pathway described above. In fact, the mechanism of action of the inventive compounds explains why these compounds have multifarious applications in treating a broad variety of clinical indications.

Activation of the second messenger pathway is a significant mediator of response to noxious stimuli and results in cellular signals that lead to, for example, acute and chronic inflammation, immune response and cancer cell growth. Although the inventive compounds may desirably inhibit other noxious stimuli not discussed, they most effectively mediate the above conditions. Signals mediated by the present second messenger pathway include, for example, those cellular responses to lipopolysaccharide (LPS) directly; T cell activation by antigen; B cell activation by antigen, cellular responses to IL-1 (mediated through the IL-1 Type I receptor but not the IL-1 Type II receptor) and TNF (Type I receptor), growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

The inventive compounds: (1) block IL-1 signal transduction through the Type I receptor as shown, for example, by preventing IL-1 and IL-1 plus PDGF-induced smooth muscle, endothelial and kidney mesangial cell proliferation; (2) suppress up-regulation of adhesion molecules as shown, for example, by blocking VCAM in endothelial cells; (3) inhibit TNF-, LPS- and IL-1 -induced metalloproteases (an inflammation model); (4) block LPS-, TNF- or IL-1-induced metalloprotease and secondary cytokine production (modeling prevention or treatment of septic shock); (5) suppress T cell and B cell activation by antigen and IL-2 and IL-4; (6) inhibit mast cell activation by immunoglobulin E (IgE); (7) are cytotoxic for transformed cells and tumor cell lines, yet not for normal cells; and (8) block signaling by IL-2, IL-4, IL-6 and IL-7 on T and B cells.

The inventive compounds also are useful as an adjuvant to inhibit toxic drug side effects (i.e., IL-2, amphoteracin B and cytoreductive therapies) mediated through the second messenger pathway. Furthermore, the compounds of the invention are able to decrease enhanced levels of a relevant PA and DAG resulting from stimulation of synaptosomes with acetylcholine and/or epinephrine. This predicts that the effects of the compounds of the invention are to both enhance the release of inhibitory neural transmitters such as dopamine, and to modulate the distal "slow current" effects of such neurotransmitters.

The inventive compounds provide a method for maintaining homeostasis in cells contacted by primary stimuli by mitigating the effects of these primary stimuli on the secondary signaling pathways invoked within seconds of a primary stimulus. For example, administration of an inventive compound in vivo or ex vivo provides a method to modify cellular behavior, the method comprising contacting cells (in vivo or ex vivo), whose behavior is to be modified, with an effective amount of an inventive compound or a pharmaceutical composition thereof wherein said method is a method to: (1) inhibit proliferation of tumor cells; (2) suppress activation of T-cells by antigen or IL-2 stimulation; (3) suppress activation of monocyte/macrophage cells by endotoxin, TNF, IL- 1 or GM-CSF stimulation; (4) suppress antibody production of B-cells in response to an antigen, IL-4 or CD40 ligand; (5) inhibit proliferation of smooth muscle cells in response to growth factors capable of stimulating said proliferation; (6) lower systemic vascular resistance conferred by endothelial cells by reducing release of hypertension-inducing substances; (7) lower systemic vascular resistance induced by endothelial cells by enhancing release of anti-hypertensive substances; (8) lower expression of adhesion molecules induced by enhancers thereof; (9) suppress activation of T-cells and macrophages by HIV, thus inhibiting viral replication; (10) inhibit proliferation of kidney mesangial cells in response to stimulation by IL-1 and/or MIP-lot and/or PDGF and/or FGF; (11) enhance resistance of kidney glomerular or tubular cells to cyclosporin A or amphotericin B; (12) prevent release of MIP-1α by IL-1, TNF, or endotoxin stimulated monocytes and macrophages; (13) prevent release of platelet activating factor by IL-1, TNF, or endotoxin treated megakaryocytes, fibroblastic cells, and macrophages; (14) prevent down-regulation of receptors for cytokines in TNF-treated hematopoietic progenitor cells; (15) suppress production of metalloproteases in IL-1- or TNF-stimulated glomerular epithelial or synovial cells; (16) enhance resistance of gastrointestinal or pulmonary epithelial cells to cytotoxic drugs or radiation; (17) enhance the antitumor effect of a non-alkylating anti-tumor agent; (18) inhibit production of osteoclast activating factor in response to IL-1; (19) inhibit degranulation in response to IgE; (20) enhance release of adrenergic neural transmitters, dopamine, norepinephrine, or epinephrine, or the neurotransmitter acetylcholine; (21) modulate post-synaptic "slow current" effects of adrenergic neurotransmitters, such as dopamine, epinephrine, or norepinephrine, or the neurotransmitter acetylcholine; (22) suppress signaling by neurotransmitters including acetyl choline, leuenkephalin and seretonin; or (23) increase seizure threshold.

Compounds of the Invention

The inventive compounds are useful therapeutic agents, inhibiting proinflammatory and neoplastic cellular signaling mechanisms, which include resolved enantiomers and/or diastereomers, hydrates, salts, solvates and mixtures thereof and have the formula:

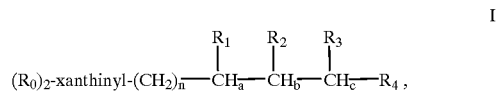

wherein $R_0$ is selected from the group consisting of hydrogen, halo, hydroxyl, amino, substituted or unsubstituted $C_{(1-10)}$ alkyl, $C_{(2-10)}$ alkenyl, cyclic or heterocyclic groups, wherein the substituents of substituted $C_{(1-10)}$ alkyl, $C_{(2-10)}$ alkenyl are other than halo; n is an integer from one to sixteen; $R_1$, $R_2$, and $R_3$ are independently selected from the group consisting of a halo; haloacetoxy; hydrogen; hydroxy; oxo; —N=C=S; —N=C=O; —O—C≡N; —C≡N; —N=N=N; and —C—$(R_5)_3$, $R_5$ being independently a halo or hydrogen, at least one $R_5$ being halo, at least one of $R_1$, $R_2$, and $R_3$ being halo, cyano, isocyano, isothiocyano, azide or haloacetoxy group; $R_4$ is hydrogen, $C_{(1-6)}$ alkyl, $C_{(1-6)}$ alkenyl, cyclo $C_{(4-6)}$ alkyl, or phenyl; one or more hydrogen atoms of $(CH_2)_n$—$CH_a$—$CH_b$—$CH_c$ may be replaced with: i) at least one of halogen atom, hydroxyl, oxo, substituted or unsubstituted $C_{(1-10)}$ alkyl, $C_{(1-10)}$ alkoxyalkyl, or $C_{(2-10)}$ alkenyl; or ii) one or more unsaturated bonds; and any two adjacent carbon atoms of $(CH_2)_n$—$CH_a$—$CH_b$—$CH_c$ may be instead separated by at least one oxygen atom.

Compounds wherein $R_2$ and $R_3$ are selected from the group consisting of halo, oxo, and hydroxyl group are preferred.

In compounds of the invention which include a halo group, a preferred halo group is chloro, bromo, or fluoro.

$R_0$ is preferably selected from the group consisting of cyclohexyl, cyclopentyl, 3-dimethylaminobutyl, ethyl, hexyl, 2-hydroxyethyl, 5-hydroxyhexyl, 3-hydroxy-n-butyl, 3-hydroxypropyl, isobutyl, isopropyl, 2-methoxyethyl, 4-methoxy-n-butyl, methyl, n-butyl, n-propyl, phenyl and t-butyl.

When one or more hydrogen atoms of $(CH_2)_n$—$CH_a$—$CH_b$—$CH_c$ is independently replaced with a substituted $C_{(1-10)}$ alkyl, $C_{(1-10)}$ alkoxyalkyl, $C_{(2-10)}$ alkenyl, cyclic or heterocyclic group; the corresponding substituents are preferably at least one member selected from the group consisting of amide, primary, secondary and tertiary amino, $C_{(2-8)}$ alkenyl, $C_{(1-8)}$ alkyl, $C_{(1-8)}$ alkoxy, $C_{(1-8)}$ hydroxyalkyl, azidyl, oxo, carboxyl, cyano, $C_{(1-8)}$ haloalkyl, isocyano, isothiocyano, phosphate, phosphonate, sulfonate, sulfone, sulfoxyl, thioamido, thiocarbonyl, thioester, thiol, thiourea and urea.

Preferred cyclic or heterocyclic groups are selected from the group consisting of anthracene, bicyclo[4.4.0]decane, bicyclo[2.2.1]heptane, bicyclo[3.2.0]heptane, bicyclo[4.1.0] heptane, bicylo[2.2.1]hexane, bicyclo[4.3.0]nonane, bicyclo [2.2.2]octane, biphenyl, cyclopentadiene, cyclopentane, cyclobutane, cyclobutene, cycloheptane, cyclohexane, cyclooctane and cyclopropane, 1,2-diphenylethane, fluorene, indene, phenyl, quinone, terphenyl, napthalene, phenanthrene, terphenyl, toluene, xylene, azetidine, benzofuran, benzothiophene, carbazole, furan, glutarimide, indole, isoquinoline, lactam, lactone, oxazole, oxetane, oxirane, phthalimide, piperidine, pyrrolidine, pyran, pyridine, pyrrole, quinoline, tetrahydrofuran, tetrahydropyran, tetrahydrothiophene, thiophene, thymine and derivatives thereof.

The invention provides a pharmaceutical composition comprising an inventive compound and a pharmaceutically acceptable excipient. The pharmaceutical composition may be formulated for oral, parenteral or topical administration to a patient.

A pharmaceutical composition may alternatively comprise one or a plurality of inventive compounds and a pharmaceutically acceptable carrier or excipient. Treatment of individuals with an inventive compound or pharmaceutical composition may include contacting with the inventive compound in vitro culture, in an extracorporeal treatment, or by administering (oral, parenteral or topical) the inventive compound or pharmaceutical composition to a subject whose cells are to be treated.

Synthesis of the Inventive Compounds

The invention includes a method for preparing inventive compounds. Exemplary preparation methods are discussed below and in the following examples.

In the inventive method, a predetermined amount of a core-containing compound is reacted with a suitable base, a solvent and a substituted halide, the substituted halide having at least one other functional group which may be substituted in a displacement reaction by the desired core-containing compound.

Preferred bases include, but are not limited to, sodium hydride, sodium amide, sodium alkoxide, lithium hydride, potassium hydride, lithium amide and potassium amide. An especially preferred base is sodium hydride. Preferred solvents may be dimethylsulfoxide, dimethylformamide, or an alcohol. Exemplary preferred alcohols include, but are not limited to, methanol, ethanol or isopropanol. Any substituted halide comprising a chain structure of the inventive compounds may be used in the preliminary reaction according to the invention. Preferred halides may be substituted halides. Preferred substituted halides include, but are not limited to, halo-substituted halides or dihalides.

The halide product, an inventive compound, having a composite structure of the core-containing compound and substituted halide, may subsequently be converted to a corresponding compound having an azido group, also an inventive compound. The halide product is reacted with a salt of hydrazoic acid to obtain an azide. Preferred salts of hydrazoic acid include, but are not limited to, potassium azide, sodium azide, or lithium azide.

In addition, a nitrile-substituted inventive compound may be prepared from the halide product by reaction with a salt of hydrogen cyanide. Preferred salts of hydrogen cyanide include, but are not limited to, potassium cyanide and sodium cyanide.

The inventive method includes an alternative process for preparing a nitrile. In this method, a core-containing compound is reacted with a suitable base, a solvent and a substituted nitrile, the substituted nitrile having at least one other functional group, which may be substituted in a displacement reaction by the desired core-containing compound.

Preferred bases may be selected from the list of bases previously discussed. An especially preferred base is potassium carbonate. Preferred solvents likewise may be selected from the foregoing list. Any substituted nitrile comprising a chain structure of the inventive compounds may be used in the preliminary reaction according to the invention. Preferred nitrites may be substituted nitrites. Preferred substituted nitrites include, but are not limited to, halo-substituted nitrites.

Treatment of the substituted azide in a reduction reaction with a suitable reducing agent produces an intermediate amine product. Exemplary reducing agents include, but are not limited to, hydrogen with palladium on carbon, hydrogen with Raney nickel, or hydrogen with platinum oxide. A corresponding inventive isothiocyanate may be prepared from the intermediate amine product by reaction with thiophosgene or a its chemical equivalent. In addition, a corresponding inventive isocyanate may be prepared from the intermediate amine product by reaction with phosgene or its chemical equivalent such as trichloromethyl chloroformate.

For some inventive compounds (e.g., bromoesters, azidoalcohols, chlorohydrins, and chloroketones) the method also includes preparation of these representative compounds having other functional groups in the side chain. Primarily, as in the other described synthetic processes, a core-containing compound is reacted with a suitable base, a solvent and a substituted olefin, the substituted olefin having at least one functional group which may be substituted in a displacement reaction by the desired core-containing compound.

Bases and solvents may again be selected from the foregoing, representative list. Any substituted olefin comprising a chain structure of the inventive compounds may be used in the preliminary reaction according to the invention. Preferred olefins may be substituted olefins. Preferred substituted olefins include, but are not limited to halo-substituted olefins.

The intermediate olefinic product is reacted with a suitable oxidizing agent to obtain an intermediate diol. Preferred oxidizing agents include, but are not limited to, osmium tetroxide. Preferred oxidizing agents, such as osmium tetroxide may require a catalytic amount of oxidizing agent in the presence of a regenerating agent. Exemplary, regenerating agents may be 4-methylmorpholine-N-oxide and trimethylamine-N-oxide. An especially preferred regenerating agent is 4-methylmorpholine-N-oxide. In a subsequent halogenation reaction, the resulting intermediate diol is converted to an inventive compound, a haloester, using a halogenating agent in the presence of an organic acid. Exemplary halogenating agents include hydrogen bromide and hydrogen chloride. Preferred organic acids may be acetic acid and propionic acid.

The haloester is reacted with a basic ester-hydrolyzing reagent to obtain a desired intermediate epoxide product. Preferred ester-hydrolyzing agents include, but are not limited to metal alkoxides and metal hydroxides. Especially preferred metal alkoxides are sodium methoxide, ethoxide, isopropoxide and pentoxide. A preferred metal hydroxide is sodium hydroxide.

Alternatively, the intermediate olefinic product may be reacted with an organic peracid to obtain a desired intermediate epoxide product. Preferred exemplary organic peracids include 3-chloroperoxybenzoic acid, peracetic acid and trifluoroperacetic acid. An especially preferred peracid is 3-chloroperoxybenzoic acid.

Other methods for preparing preferred inventive compounds include the following general processes.

1) An inventive azidoalcohol may be prepared from the intermediate epoxide product by reaction with a salt of hydrazoic acid. Exemplary salts of hydrazoic acid include, but are not limited to, potassium azide, sodium azide, or lithium azide.

2) An inventive halohydrin may be prepared from the intermediate epoxide product by reaction with a suitable halogenating reagent. Although other halogenating reagents are within the scope of the invention, a preferred reagent is oxalyl chloride in dimethylsulfoxide.

3) An inventive haloketone may be prepared from the halohydrin product by reaction with a suitable oxidizing reagent. Oxalyl chloride and triethylamine in dimethylsulfoxide is an exemplary oxidizing reagent although other reagents are within the scope of the invention. A pictorial representation of the foregoing methods of the invention is provided in the following general schematic.

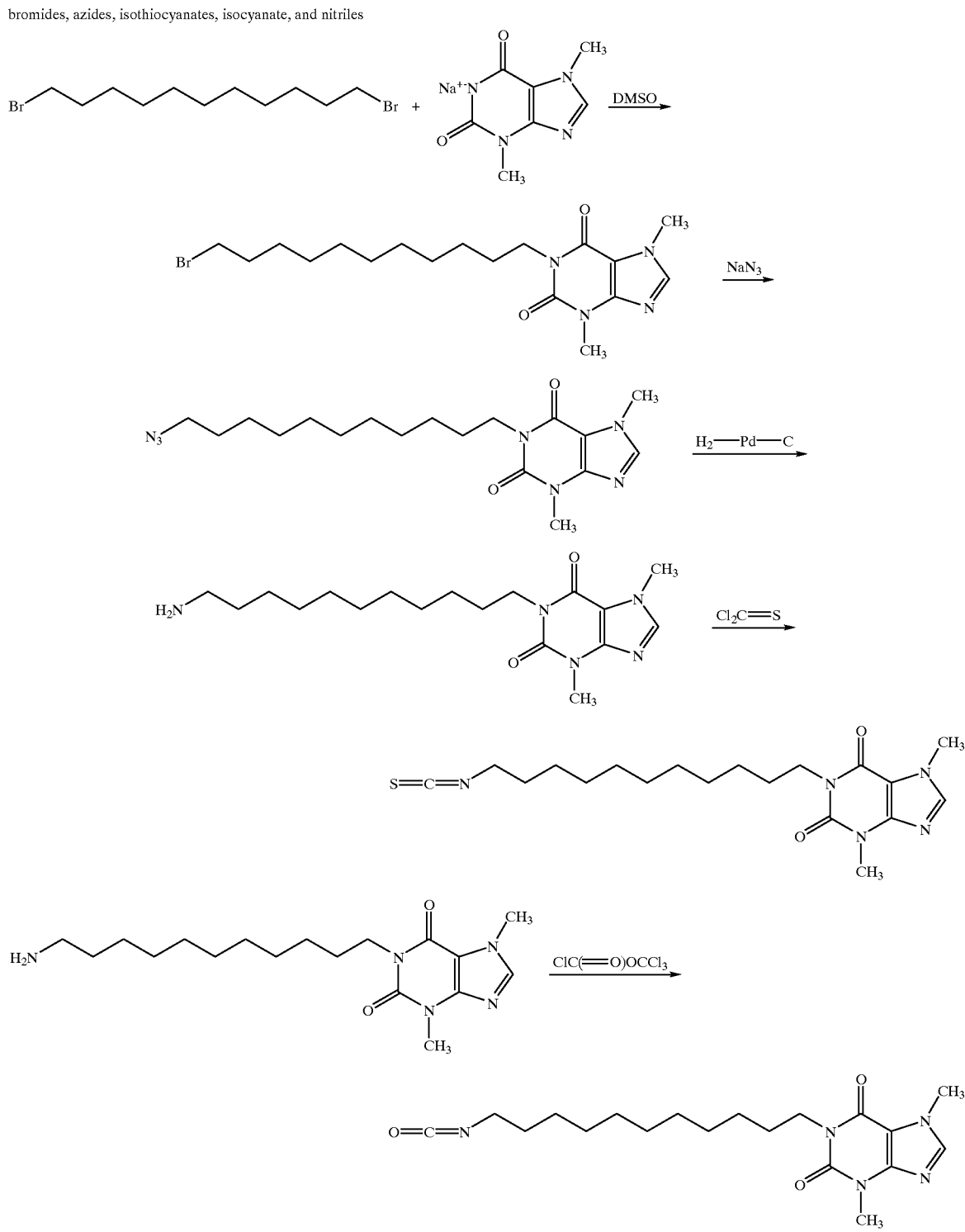

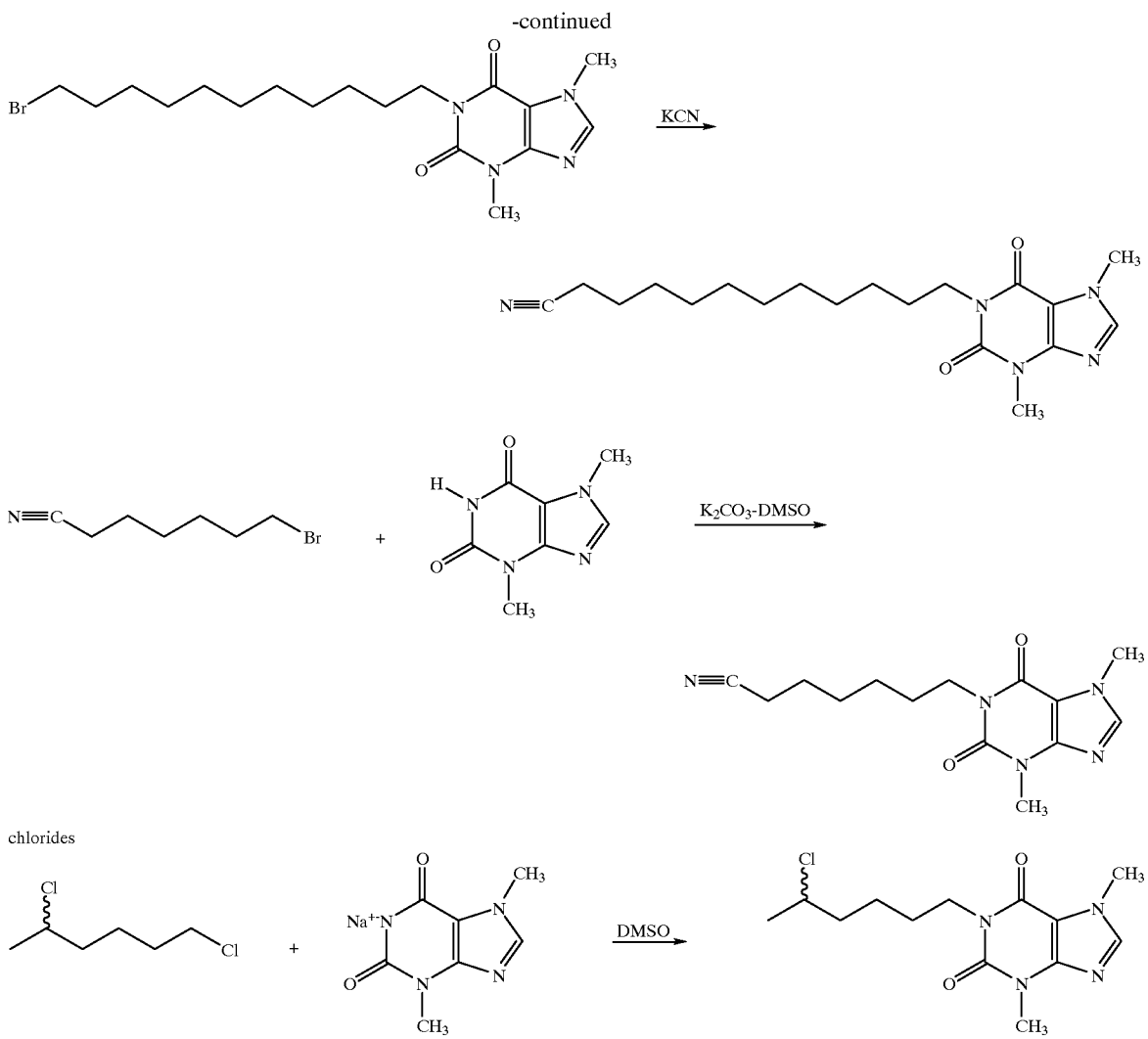

The compounds of the invention may be provided as enantiomeric or diastereomeric mixtures or in resolved or partially resolved forms. Standard procedures are used for resolving optical isomers. Different enantiomeric variants (e.g., stereoisomers and chiral forms) of the inventive compound may have different drug activities, based upon their differential ability to inhibit PAPH and LPAAT. An optical isomer, substantially free of the corresponding enantiomer and/or diasteromers, is at least about 85% of a relevant optical isomer, preferably at least about 95% relevant optical isomer and especially at least about 99% or higher relevant optical isomer. Most preferably an amount of other optical forms in undetectable.

Exemplary, preferred compounds of the invention include both R and S enantiomers and racemic mixtures of the following compounds:

1514 1-(7-acetoxy-8-bromooctyl)-3,7-dimethylxanthine

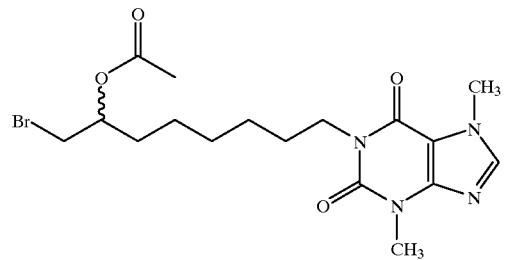

1517 1-(6-azido-5-hydroxyhexyl)-3,7-dimethylxanthine

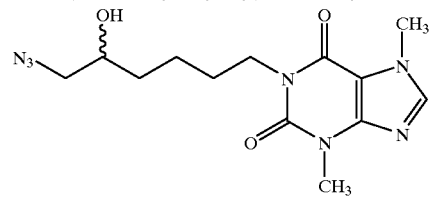

1525 1-(6-chlorohexyl)-3,7-dimethylxanthine

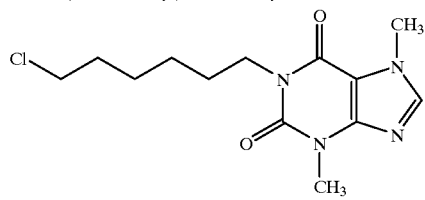

1527 1-[6-(chloroacetoxy)hexyl]-3,7-dimethylxanthine

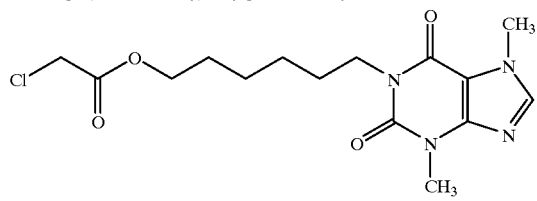

1529 1-[5-(chloroacetoxy)hexyl]-3,7-dimethylxanthine

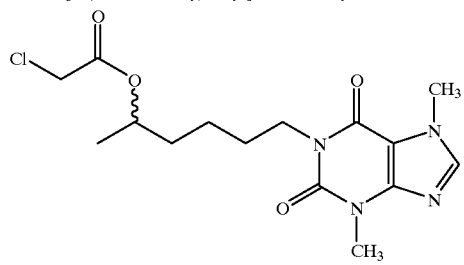

1577 1-(5-fluorohexyl)-3,7-dimethylxanthine

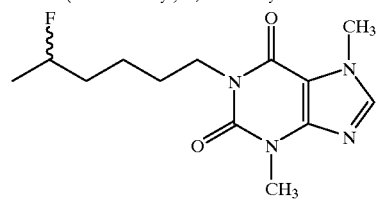

1583 1-(9-acetoxy-10-bromodecyl)-3,7-dimethylxanthine

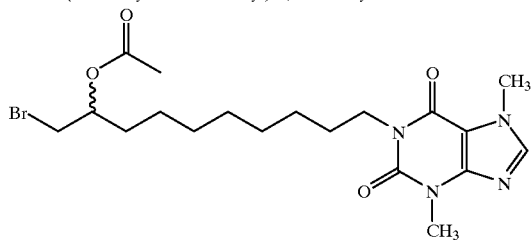

1589 1-(6-bromohexyl)-3,7-dimethylxanthine

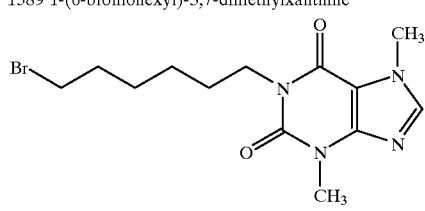

1595 1-(6-chloro-5-oxohexyl)-3,7-dimethylxanthine

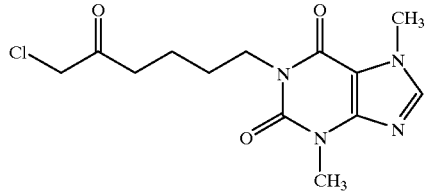

2519 1-(5-isothiocyanatohexyl)-3,7-dimethylxanthine

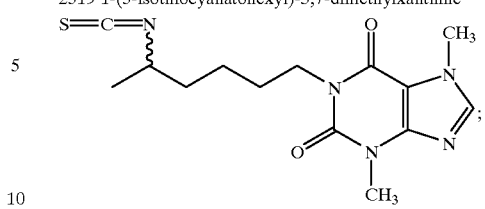

2557 1-(6-azidohexyl)-3,7-dimethylxanthine

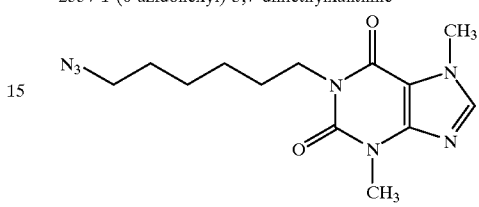

2580 1-(6-chloro-5-hydroxyhexyl)-3,7-dimethylxanthine

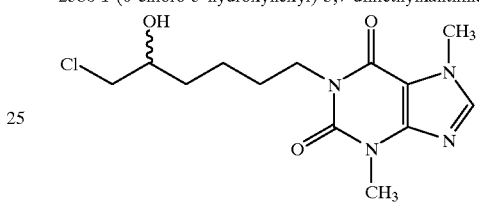

2581 1-(6-bromo-5-hydroxyhexyl)-3,7-dimethylxanthine

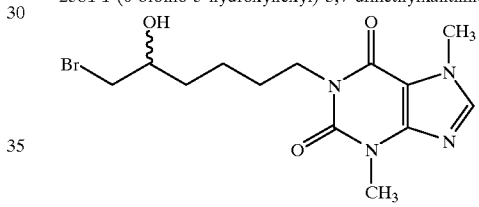

2590 1-(11-chloro-10-hydroxyundecyl)-3,7-dimethylxanthine

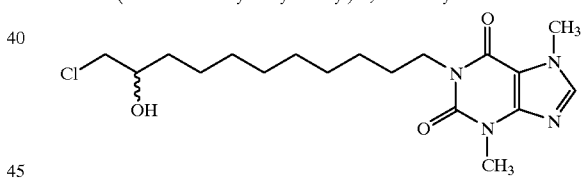

2591 1-(11-chloro-10-oxoundecyl)-3,7-dimethylxanthine

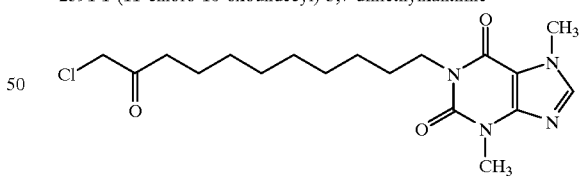

2599 1-(14-bromo-13-hydroxytetradecyl)-3,7-dimethylxanthine

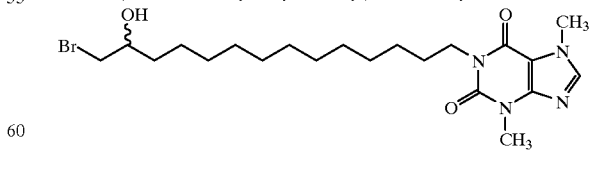

3502 1-(9-bromononyl)-3,7-dimethylxanthine

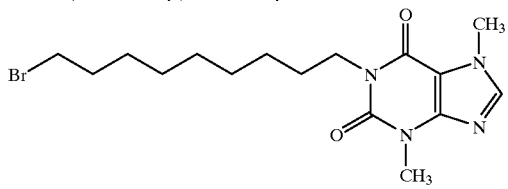

3507 1-(9-azidononyl)-3,7-dimethylxanthine

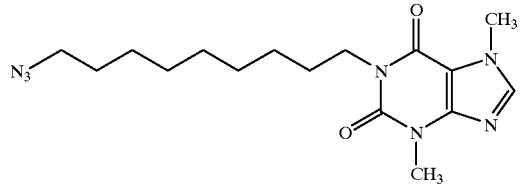

3538 1-(9-isothiocyanatononyl)-3,7-dimethylxanthine

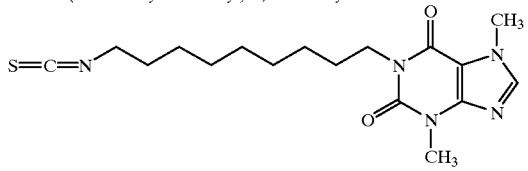

3443 1-(11-bromoundecyl)-3,7-dimethylxanthine

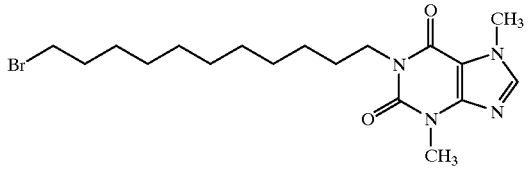

3544 1-(11-azidoundecyl)-3,7-dimethylxanthine

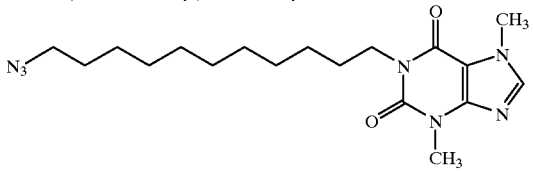

3555 1-(6,6,6-trifluoro-5-hydroxyhexyl)-3,7-dimethylxanthine

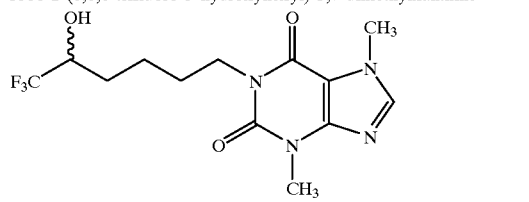

3558 1-(11-isothiocyanatoundecyl)-3,7-dimethylxanthine

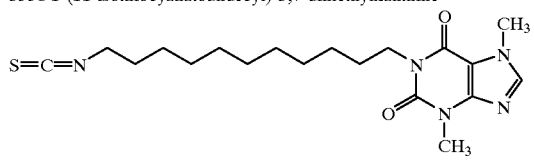

3567 1-(11-azido-10-hydroxy undecyl)-3,7-dimethylxanthine

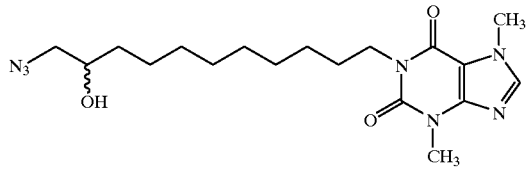

3597 1-(5-chlorohexyl)-3,7-dimethylxanthine

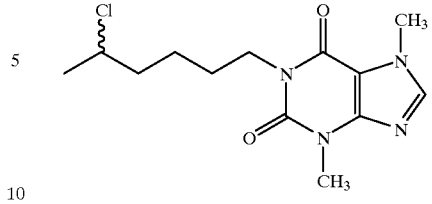

Pharmaceutical Formulations

A suitable formulation will depend on the nature of the disorder to be treated, the nature of the medicament chosen, and the judgment of the attending physician. In general, the inventive compounds are formulated wither for injection or oral administration, although other modes of administration such as transmucosal or transdermal routes may be employed. Suitable formulations for these compounds can be found, for example, in Remington's Pharmaceutical Sciences (latest edition), Mack Publishing Company, Easton, Pa.

The inventive compounds are their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder of pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for parenteral administration is preferably from about 0.001 mg/kg to about 40 mg/kg, more preferably from about 0.01 mg/kg to about 20 mg/kg of an inventive compound or a pharmaceutically acceptable salt thereof, calculated as the free base.

The inventive compounds may also be administered orally. The daily dosage regimen for oral administration is suitably from about 0.1 mg/kg to about 1000 mg/kg per day. The active ingredient may be administered from 1 to 6 times a day, sufficient to exhibit activity.

The inventive compounds may be administered by inhalation (e.g., intranasal or oral). Appropriate dosage forms include an aerosol or a metered dose inhaler, as prepared by conventional techniques. The daily dosage is suitably from about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

While dosage values will vary, therapeutic efficacy is achieved when the compounds of the invention are administered to a human subject requiring such treatment as an effective oral, parenteral, or intravenous dose of about 50 mg to about 5000 mg per day, depending upon the weight of the patient. It is to be understood, however, that for any particular subject or mode of administration, specific dosage regimens should be adjusted to the individual's need and to the professional judgment of the person administering or supervising the administration of the inventive compounds.

The following examples, which should not be regarded as limiting in any way, illustrate the invention.

EXAMPLE 1

This example illustrates the synthesis of several compounds that are used as intermediates for the synthesis of other compounds.

1-(5,6-Oxidohexyl)-3,7-dimethylxanthine was synthesized and used as an intermediate for synthesizing inventive compounds nos. 1517 and 1595 as described in examples 2 and 3 below. A mixture of 1-bromo-5-hexene (10.7 g, 66 mmol), sodium hydride (1.58 g, 66 mmol), and 3,7-dimethylxanthine (11.9 g, 66 mmol) in dimethylsulfoxide (100 ml) was stirred for 43 hr. The solution was treated with water (200 ml) and then extracted with dichloromethane (3×80 ml). The combined extracts were washed with water (3×100 ml), dried over magnesium sulfate, and then the solvent was evaporated under vacuum to give 1-(5-hexenyl)-3,7-dimethylxanthine (17 g, 98% yield) as a white powder.

To 1-(5-hexenyl)-3,7-dimethylxanthine (1.07 g, 4.1 mmol), synthesized above, and 4-methylmorpholine-N-oxide (1.44 g, 12.3 mmol) in water (20 ml) and acetone (10 ml) was added 2.5% solution of osmium tetroxide in t-butanol (6 drops). After stirring for 48 hr, the mixture was treated with 20% aqueous sodium dithionite solution (20 ml). After 2 min, the mixture was extracted with 25% ethanol-dichloromethane (3×30 ml). The combined extracts were dried over magnesium sulfate and the solvents were evaporated under vacuum to give 1-(5,6-dihydroxyhexyl)-3,7-dimethylxanthine (750 mg, 62% yield) as a white powder.

To 1-(5,6-dihydroxyhexyl)-3,7-dimethylxanthine (1.0 g, 3.38mmol), prepared above, was added 30% hydrogen bromide-acetic acid (3.4 ml) over 30 sec and the resulting mixture was stirred until all of the solid had dissolved (2.5 hr). The solution was poured carefully over a mixture of sodium bicarbonate (12 gm) and ice water (50 ml). After carbon dioxide evolution had subsided, the mixture was extracted with dichloromethane (3×25 ml). The combined extracts were dried over magnesium sulfate and the solvent was evaporated under vacuum to give 1-(5-acetoxy-6-bromohexyl)-3,7-dimethylxanthine (1.3 g, 96% yield) as a viscous oil which was dissolved in methanol (5 ml). A 1M solution of sodium methoxide in methanol (3.9 ml) was added over 30 sec. After stirring for 20 min, the solution was treated with water (20 ml) and then extracted with dichloromethane (3×15 ml). The combined extracts were dried over magnesium sulfate and the solvents were evaporated under vacuum to give 1-(5,6-oxidohexyl)-3,7-dimethylxanthine (900 mg, 100% yield) as white crystals.

1-(6-Hydroxyhexyl)-3,7-dimethylxanthine was used as an intermediate for the synthesis of inventive compounds nos. 1525 (example 4), 1527 (example 5), and 1589 (example 6). A mixture of theobromine (1.0 g, 5.5 mmol) and 50% sodium hydride in oil (264 mg, 5.5 mmol) in dimethylsulfoxide (20 ml) was stirred for 50 min and then 6-bromo-1-hexanol (1.0 g, 5.5 mmol) was added. After stirring for 18 hr, the solution was treated with water (50 ml) and then extracted with hexane (2×25 ml). The aqueous phase was extracted with 25% ethanol-dichloromethane (3×35 ml). The combined ethanol-dichloromethane extracts were dried over magnesium sulfate and then the solvents were evaporated under vacuum. The remaining dimethylsulfoxide was removed by distillation under full pump vacuum to give 1-(6-hydroxyhexyl)-3,7-dimethylxanthine (1.4 g, 91% yield) as a white powder.

1-(5-Hydroxyhexyl)-3,7-dimethylxanthine was used as an intermediate for the synthesis of inventive compounds nos. 1529 (example 7) and 1577 (example 8). To a solution of 1-(5,6-oxohexyl)-3,7-dimethylxanthine (250 mg, 0.9 mmol), prepare as provided above, in absolute ethanol (15 ml) was added sodium borohydride (85 mg, 2.25 mmol), and the solution was heated at 90° C. for 2 hr. After cooling to ambient temperature, the solution was treated with half-saturated aqueous ammonium chloride solution (30 ml). The mixture was extracted with 25% ethanol-dichloromethane (4×15 ml). The combined extracts were dried over magnesium sulfate and the solvents were evaporated under vacuum to give 1-(5-hydroxyhexyl)-3,7-dimethylxanthine (250 mg, 100% yield).

1-(5-aminohexyl)-3,7-dimethylxanthine was used as an intermediate for the synthesis of inventive compound no. 2519 (example 10). To a solution of pentoxifylline (1.39 g, 5 mmol) and ammonium acetate (3.85 g, 50 mmol) in methanol (50 ml) was added sodium cyanoborohydride (628 mg, 10 mmol). After stirring for 24 h, the mixture was treated with dichloromethane (50 ml) and water (50 ml). The aqueous layer was treated with saturated aqueous ammonium chloride solution (20 ml) and stirred for 15 min. After treatment with 30% aqueous ammonium hydroxide solution (30 ml), the solution was extracted with 25% ethanol-dichloromethane (3×35 ml). The combined extracts were dried over magnesium sulfate and then the solvents were evaporated under vacuum to give 1-(5-aminohexyl)-3,7-dimethylxanthine (950 mg, 68% yield).

1-(9,10-Dihydroxydecyl)-3,7-dimethylxanthine was used as an intermediate for the synthesis of inventive compound no. 1583 (example 11). To a solution of 9-decene-1-ol (3.0 g, 19.2 mmol) in dichloromethane (100 ml) at 0° C. was added methanesulfonyl chloride (2.20 g, 19.2 mmol) followed by triethylamine (2.91 g, 28.8 mmol) After stirring for 15 min at 0° C., the reaction was allowed to warm to room temp. After stirring for 2 hr, the reaction was poured into water (100 ml) and extracted with dichloromethane (3×60 ml). The combined organic layers were dried over sodium sulfate and the volatiles were evaporated under vacuum to give 9-decene-1-methanesulfonate (4.52 g, 100% yield) which was used without further purification. To a suspension of sodium hydride (461 mg, 19.2 mmol) in dimethylsulfoxide (30 ml) was added theobromine (3.45 g, 19.2 mmol).

After stirring for 15 min, 9-decene-1-methanesulfonate (2.25 g, 11 mmol) was added and the mixture was stirred at room temperature for 18 hr and then at 100° C. for 40 min. After cooling to ambient temperature, the mixture was poured into water (100 ml) and extracted with dichloromethane (3×50 ml). The combined organic layers were washed with saturated aqueous sodium chloride solution (60 ml) and dried over magnesium sulfate. The solvent was evaporated under vacuum to give a solid which was recrystallized (ether) to give 1-(9-decenyl)-3,7-dimethylxanthine (3.40 g, 56% yield).

A solution of 1-(9-decenyl)-3,7-dimethylxanthine (3.2g, 10.1 mmol), prepared above, 4-methylmorpholine-N-oxide (1.41 g, 12 mmol) and 2.5% osmium tetroxide in t-butanol (3 drops) in acetone (40 ml) and water (10 ml) was stirred for 24 hr. After the addition of saturated sodium dithionite solution (5 ml) the mixture was stirred for 15 min. The mixture was extracted with 25% ethanol-dichloromethane (4×50 ml). The combined organic layers were dried over sodium sulfate and the solvents were evaporated under vacuum to give a solid which was recrystallized (ethanol) to give 1-(9,10-dihydroxydecyl)-3,7-dimethylxanthine (3.30 g, 93% yield).

1-(7,8-Dihydroxyoctyl)-3,7-dimethylxanthine was used as an intermediate for the synthesis of inventive compound no. 1514 (example 12). To a suspension of sodium hydride (580 mg, 24.2 mmol) in dimethylsulfoxide (100 ml) was added theobromine (3.96 g, 22.0 mmol). After stirring for 30 min, 8-bromo-1-octene (3.96 g, 22 mmol) was added and the mixture was stirred for 16 hr. The mixture was poured into water (200 ml) and extracted with dichloromethane (3×50 ml). The combined organic layers were washed with saturated aqueous sodium chloride solution (50 ml), dried over sodium sulfate, and the solvent was evaporated under vacuum to give 1-(7-octenyl)-3,7-dimethylxanthine (6.22 g, 97% yield) as an oil which solidified upon standing.

A solution of 1-(7-octenyl)-3,7-dimethylxanthine (1.00 g, 4.5 mmol), prepared above, 4-methylmorpholine-N oxide (553 mg, 4.7 mmol), and 2.5% osmium tetroxide in t-butanol (3 drops) in acetone (25 ml) and water (20 ml) was stirred for 4 days. After addition of saturated aqueous sodium hydrosulfite solution (10 ml), the mixture was stirred for 30 min and water (50 ml) was added. The mixture was extracted with 20% ethanol-dichloromethane (3×50 ml) and the solvents were evaporated under vacuum to give a solid which was recrystallized (ethanol) to give 1-(7,8-dihydroxyoctyl)-3,7-dimethylxanthine (726 mg, 63% yield) as a white solid.

EXAMPLE 2

This example illustrates a method for synthesis of inventive compound no. 1517 (see above for name and chemical structure). A mixture of (5,6-oxidohexyl)-3,7-dimethylxanthine (1.00 g, 3.6 mmol), prepared in Example 1, and sodium azide (818 mg, 12.6 mmol) in acetone (10 ml) and water (10 ml) was refluxed for 5 hr. After cooling to ambient temperature the mixture was poured into water (10 ml) and extracted with chloroform (3×30 ml). The combined organic layers were washed with water (20 ml) and saturated aqueous sodium chloride solution (20 ml) and then dried over sodium sulfate. After evaporation of the solvents under vacuum, the solid was recrystalized (chloroform-ethyl ether) to give compound no. 1517 (617 mg, 53% yield).

EXAMPLE 3

This example illustrates the synthesis of inventive compound no. 1595. To a solution of dimethylsulfoxide (0.390 g, 5.00 mmol) in dichloromethane (20 ml), at −60° C., was added oxalyl chloride (0.634 g, 5.00 mmol). After stirring for 5 min, 1-(5,6-oxidohexyl)-3,7-dimethylxanthine(0.548 g, 2.00 mmol), prepared in Example 1, and methanol (0.0064 g, 0.20 mmol) were added. After stirring for 30 min at −60° C., triethylamine (1.01 g, 10.0 mmol) was added. After stirring at −60° C. for 10 min, the mixture was warmed to 25° C. over 30 min and then washed with saturated aqueous ammonium chloride solution (30 ml), with water (30 ml), and with saturated aqueous sodium chloride solution (30 ml). The organic phase was dried over magnesium sulfate and the solvent was evaporated under vacuum to give a residue which was purified by chromatography (silica, methanol-dichloromethane) to afford compound no. 1595 (0.38 g, 62%yield) as a cream solid.

EXAMPLE 4

This example illustrates the synthesis of inventive compound no. 1525. A solution of 1-(6-hydroxyhexyl)-3,7-dimethylxanthine (1 g, 3.6 mmol), prepared in Example 1, and triphenylphosphine (1.2 g, 4.6 mmol) in carbon tetrachloride (20 ml) was refluxed for 12 hr. The excess carbon tetrachloride was evaporated under reduced pressure. The crude product was purified by flash chromatography (silica gel, 40% hexane-ethylacetate) to give inventive compound no. 1525 (0.56 g, 53% yield).

EXAMPLE 5

This example illustrates the synthesis of inventive compound no. 1527. A solution of the chloroacetyl chloride (339 mg, 3 mmol) in dichloromethane (5 ml) was added dropwise at 0° C. to a solution of 1-(6-hydroxyhexyl)-3,7-dimethylxanthine (560 mg, 2 mmol), prepared in Example 1, and triethylamine (607.2 mg, 6 mmol) in dichloromethane (5 ml). After warming to ambient temperature, the mixture was stirred for 12 hr and then saturated aqueous sodium bicarbonate solution (5 ml) was added. The mixture was extracted with dichloromethane (3×50 ml). The combined organic extracts were washed with 1% aqueous hydrogen chloride (15 ml), with water (15 ml), and with saturated sodium chloride solution (15 ml). After drying over magnesium sulfate, the solvent was evaporated under vacuum. The residue was purified by flash chromatography (silica gel, 20% hexane-ethyl acetate) to give compound no. 1527 (296 mg, 50% yield).

EXAMPLE 6

This example illustrates the synthesis of inventive compound no. 1589. Triphenylphosphine (1.2 g, 4.6 mmol) was added in portions to a solution of 1-(6-hydroxyhexyl)-3,7-dimethylxanthine (I g, 3.6 mmol), prepared in Example 1 above, and carbon tetrabromide (1.52g; 4.6 mmol) in dichloromethane. After stirring for 30 minutes, the solvent was evaporated under reduced pressure. The crude product was purified by flash chromatography (silica gel, 40% hexane-ethyl acetate) to give compound no. 1589 (0.70 g, 59% yield).

EXAMPLE 7

This example illustrates the synthesis of inventive compound no. 1529. To a solution of the 1-(5-hydroxyhexyl)-3,7-dimethylxanthine (1.12 g, 4 mmol), prepared in Example 1, and triethylamine (809.6 mg; 8 mmol) in dichloromethane (10 ml) was added a solution of the chloroacetyl chloride (678 mg; 3 mmol) in dichloromethane (10 ml)

dropwise at 0° C. After warming to ambient temperature and stirring overnight, saturated aqueous sodium bicarbonate solution (10 ml) was added and the mixture was extracted with dichloromethane (3×75 ml). The combined organic extracts were washed with 1% aqueous hydrogen chloride (30 ml), with water (30 ml), and with saturated sodium chloride solution (30 ml). After drying over magnesium sulfate, the solvent was evaporated under reduced pressure. The residue was purified by flash chromatography (silica gel, 20% hexane-ethyl acetate) to give inventive compound no. 1529 (560 mg, 49% yield).

EXAMPLE 8

This example illustrates the synthesis of inventive compound no. 1577. A mixture of 1-(5-hydroxyhexyl)-3,7-dimethylxanthine, prepared in Example 1, and 70% hydrogen fluoride-pyridine solution in a polypropylene bottle was heated at 40–50° C. for 20 hr. After cooling to ambient temperature, saturated aqueous sodium bicarbonate solution (50 ml) was added. The mixture was extracted with dichloromethane (3×40 ml) and the combined extracts were dried over sodium sulfate. After evaporation of the solvent under a stream of nitrogen, the residue was purified by chromatography (silica, ethyl acetate) to give compound no. 1577 (150, 21% yield).

EXAMPLE 9

This example illustrates the synthesis of inventive compound no. 2557. To a stirred mixture of 1-(6-bromohexyl)-3,7-dimethylxanthine, prepared in Example 6 above, (115 mg, 0.33 mmol) and 25% aqueous solution of sodium azide (42.9 mg, 0.66 mmol) was added tetrabutylammonium bromide (5.3 mg, 0.0165 mmol). After heating at 100° C. for 12 hr, the mixture was cooled to room temperature and then extracted with dichloromethane (3×50 ml). The combined organic extracts were washed with saturated aqueous sodium chloride solution (50 ml), dried over magnesium sulfate, and concentrated under reduced pressure. The residue was purified by flash chromatography (silica, ethyl acetate) to give inventive compound no. 2557 (80 mg, 88% yield).

EXAMPLE 10

This example illustrates the synthesis of inventive compound no. 2519. To a solution of 1-(5-aminohexyl)-3,7-dimethylxanthine (0.2 g, 0.7 mmol), sodium bicarbonate (0.24 g, 2.8 mmol), and dichloromethane (2 ml) was added thiophosgene (0.081 ml, 1.1 mmol) dropwise. After stirring for 18 hr, the reaction mixture was poured into 15% aqueous ammonium hydroxide solution (15 ml). After stirring for 20 min, the solution was extracted with dichloromethane (3×15 ml). The combined organic phases were dried over sodium sulfate and the solvent was evaporated under vacuum to give compound no. 2519 (0.21 g, 91% yield) as a white solid.

EXAMPLE 11

This example illustrates the synthesis of inventive compound no. 1583. A mixture of 1-(9, 10-dihydroxydecyl)-3, 7-dimethylxanthine ( 2.11 g, 6 mmol) and 30% hydrogen bromide-acetic acid (3.6 ml, 18 mmol) was stirred for 90 min. The solution was poured into a mixture of sodium bicarbonate (5 g), water (40 ml), and dichloromethane (50 ml). After 10 min of vigorous stirring, the layers were separated and the aqueous layer was extracted with dichloromethane (2×50 ml). The combined organic layers were dried over sodium sulfate and the solvent was evaporated under vacuum to give compound no. 1583 (2.72 g, 100% yield).

EXAMPLE 12

This example illustrates the synthesis of inventive compound no. 1514. A mixture of 1-(7, 8-dihydroxyoctyl)-3,7-dimethylxanthine ( 2.11 g, 6 mmol) and 30% hydrogen bromide-acetic acid (3.58 ml, 18 mmol) was stirred for 90 min. The solution was poured into a well stirred mixture of sodium bicarbonate (4 g), water (50 ml), and dichloromethane (30 ml). After 10 min of vigorous stirring the layers were separated and the aqueous layer was extracted with dichloromethane (2×50 ml). The combined organic layers were dried over sodium sulfate) and the solvent was evaporated under vacuum to give inventive compound no. 1514 (2.51 g, 94% yield).

EXAMPLE 13

This example illustrates data regarding proliferative activity of various inventive compounds for inducting CMV promoter activity. The CMV promoter assay measures gene transcription and translation activity wherein any active compounds will have cytotoxic activity to inhibit cellular protein synthesis machinery in transformed (adenovirus) cells. Each compound was tested and the data is listed in Table I below. 2519 was the most cytotoxic compound tested.

TABLE 1

| Compound | $IC_{50}(\mu M)$ |
|---|---|
| 1514 | >500 |
| 1517 | >500 |
| 1525 | >500 |
| 1527 | 200 |
| 1529 | 100 |
| 1577 | >500 |
| 1583 | >500 |
| 1589 | 125 |
| 1595 | 20 |
| 2519 | 10 |

EXAMPLE 14

This example shows the effects of three inventive compounds on inhibition of mast cell degranulation by the serotonin release assay, which measures mast cell degranulation, an early-phase reaction to allergen challenge. Mast cells grown in tissue culture were first loaded with $^3H$ serotonin, which was incorporated into the granules in the cells. The mast cells were sensitized with antigen specific monoclonal IgE, and then triggered to degranulate with the specific antigen (dinitrophenol bound to BSA(DNP)). When cells degranulate, $^3H$ serotonin was released into the medium, and measured directly. The ability of the inventive compounds to inhibit the degranulation response was determined by the decrease in $^3H$ serotonin released in the presence of drug and was represented as % INHIBITION. The $IC_{50}$ of any given compound was experimentally determined by the ability of that compound to inhibit degranulation by 50%.

Procedurally, the serotonin release assay seeded $2 \times 10^5$ cells in 0.5 ml medium in duplicate for spontaneous release, IgE+DNP, IgE+DNP+EtOH (vehicle control), and inventive compounds. One $\mu Ci$ [$^3H$]-Serotonin/ml (i.e., 0.5 $\mu Ci$/well) (NEN Research Products, cat.# NET-398 Hydroxytryptamine Binoxalate, 5-[1,2-$^3$H(N)]-(Serotonin Binoxalate, [1,2-$^3$H(N)]-)) and 1 µl/ml IgE was added. The cells were incubated for 18 hours at 37° C. in 5% $CO_2$, washed twice with 0.5 Isotonic Buffer (25 mM disodium PIPES pH 7.1, 100 mM NaCl, 5 mM KCl, 5 mM glucose, 0.4 mM $MgCl_2$, 0.1% BSA), and sterile filtered. 250 µl Isotonic Buffer was added per will and the plates were equilibrated in an incubator for about 10 minutes.

An inventive compound was added and cells were activated with 40 ng/ml DNP-BSA (1 mg/ml diluted 1:200 in Isotonic Buffer) for 45 minutes using 2 µl/250 µl. Spontaneous release was determined in incubated cells with 250 µl Isotonic Buffer for 45 minutes, the reaction being stopped by removing supernatant and centrifuging at ~4000 rpm in a microfuge for 15 seconds to remove any detached cells. Released radiolabled sertonin was counted. To determine amount of $^3$H-serotonin incorporated into the cells Isotonic Buffer was removed and cells were lysed by adding 250 µl 1% Triton-X100 in PBS. The lysed cells were then added to 5 ml scintillation fluid, the plates were washed twice with Triton/PBS, and the washes were added to the scintillation tube. The percent serotonin release was calculated by dividing the amount of released serotonin by the sum of incorporated plus released serotonin and correcting for spontaneous released serotonin. Compound inhibition was calculated by dividing the percent serotonin release in the presence of an inventive compound by the percent serotonin release in the absence of the inventive compound.

Table 2 below shows the results of three inventive compounds (see above for chemical names and structures.)

TABLE 2

| Compound | % Inhibition | Concentration (µM) |
|---|---|---|
| 1577 | 46% | 100 |
| 1589 | 53% | 100 |
| 1595 | 88% | 100 |
| 1595 | 44% | 50 |

These data indicate that 1595 is useful as an effective asthma therapeutic agent.

EXAMPLE 15

This example tests inventive compounds nos. 1514, 1517, 1525, 1527, 1529, 1577, 1583, 1595, and 2519 in an assay to determine whether they inhibit proliferation of peripheral blood mononuclear cells (PBMC) in response to allogeneic stimulation. This in vitro mixed MLR assay is useful in predicting biologic activity of an inventive compound. Procedurally, PBMC were obtained by drawing whole blood from healthy volunteers in a heparinized container, the whole blood samples diluted with an equal volume of hanks balanced salt solution (HBSS).

This mixture was layered on a sucrose density gradient, such as a Ficoll-Hypaque® gradient (specific gravity 1.08), and centrifuged (1000×g) for 25 minutes at no warmer than room temperature. PBMC were obtained from a band at a plasma-Ficoll interface, separated and washed at least twice in a saline solution, such as HBSS. Contaminating red cells were lysed, for example, by ACK lysis for 10 minutes at 37° C., and the PBMC were washed twice in HBSS. The pellet of purified PBMC was resuspended in complete medium, such as RPMI 1640 plus 20% human inactivated serum.

Proliferative response of PBMC to allogeneic stimulation was determined in a two-way MLR performed in a 96-well microtiter plate. Approximately 105 test-purified PBMC in 200 µl complete medium were co-cultured with approximately 105 autologous (control culture) or allogeneic (stimulated culture) PBMC. Allogeneic cells were from HLA disparate individuals. Varying doses of compounds were added simultaneously upon addition of cells to the microtiter plate. The cultures were incubated for 6 days at 37° C. in a 5% $CO_2$ atmosphere, after which time, tritiated thymidine was added (for example, 1 µCi/well of 40 to 60 Ci/mmole) and proliferative inhibition was assessed by determining amount of tritiated thymidine taken up, using liquid scintillation counting.

Results shown in FIG. 1 are a bar graph of $IC_{50}$ values for ten inventive compounds (see Table 1 above for chemical names). Inventive compounds nos. 1595 and 2519 have dose-response activity in this immune modulating activity assay procedure with $IC_{50}$'s below of 10 µM, at levels easily achievable in vivo.

Figure 2:
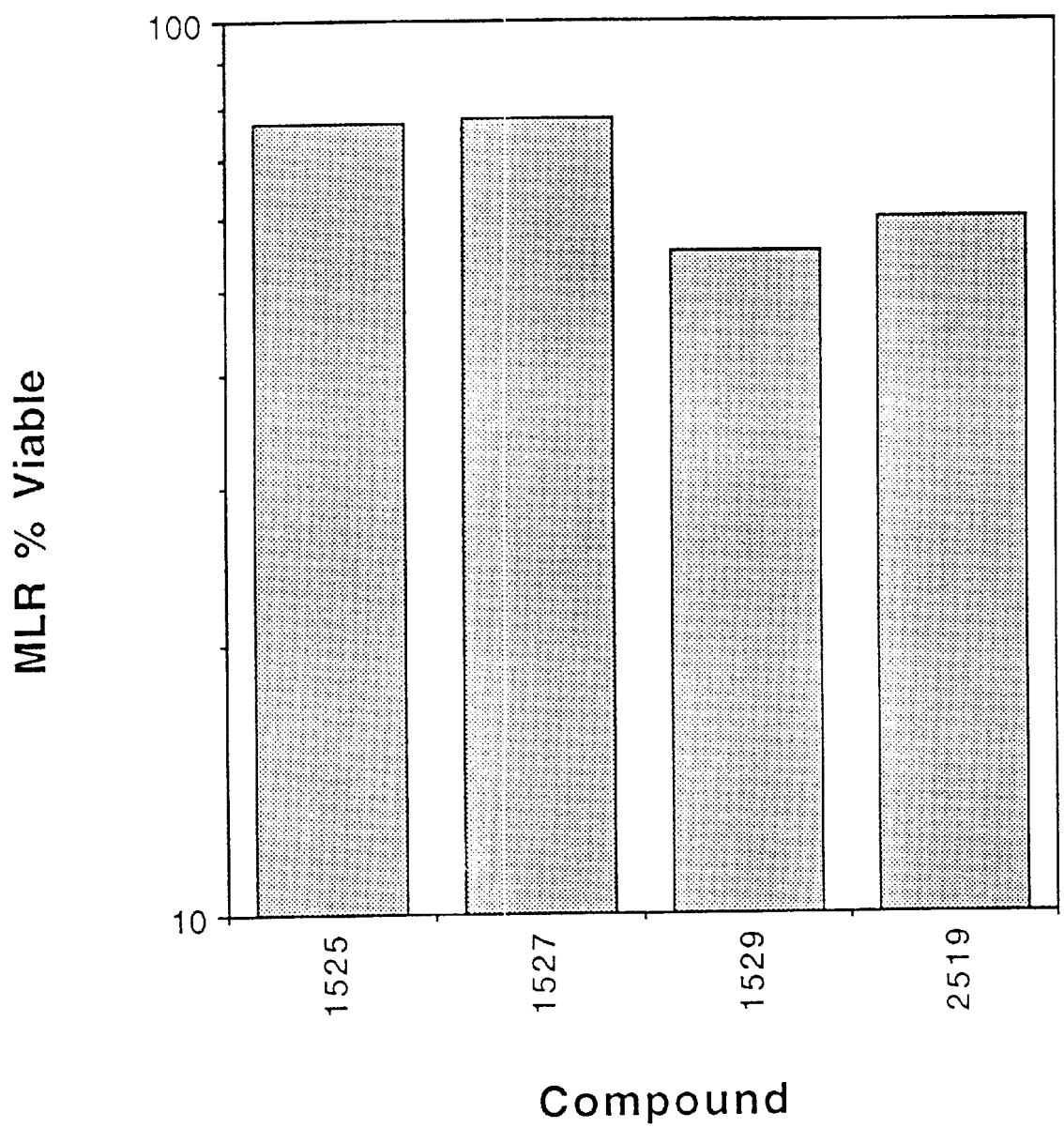
FIG. 2 shows a bar graph of the percent viable cells in mixed lymphocyte assay culture after six days of incubation with compounds of the invention.

FIG. 2 shows a bar graph of the percent viable cells in mixed lymphocyte assay culture after six days of cell culture. Control cells that have not been exposed to an inventive compound are generally 78 to 85% viable under such culture conditions. For this graph, all of the compounds were present at 100 µM, which was usually well above their $IC_{50}$ concentration in this assay (see FIG. 1). One of the most potent inventive compounds, 2519, exhibited marginal cytotoxic effects at 100 µM. This concentration is well above its $IC_{50}$ value, indicating the presence of a significant therapeutic window.

Figure 3:
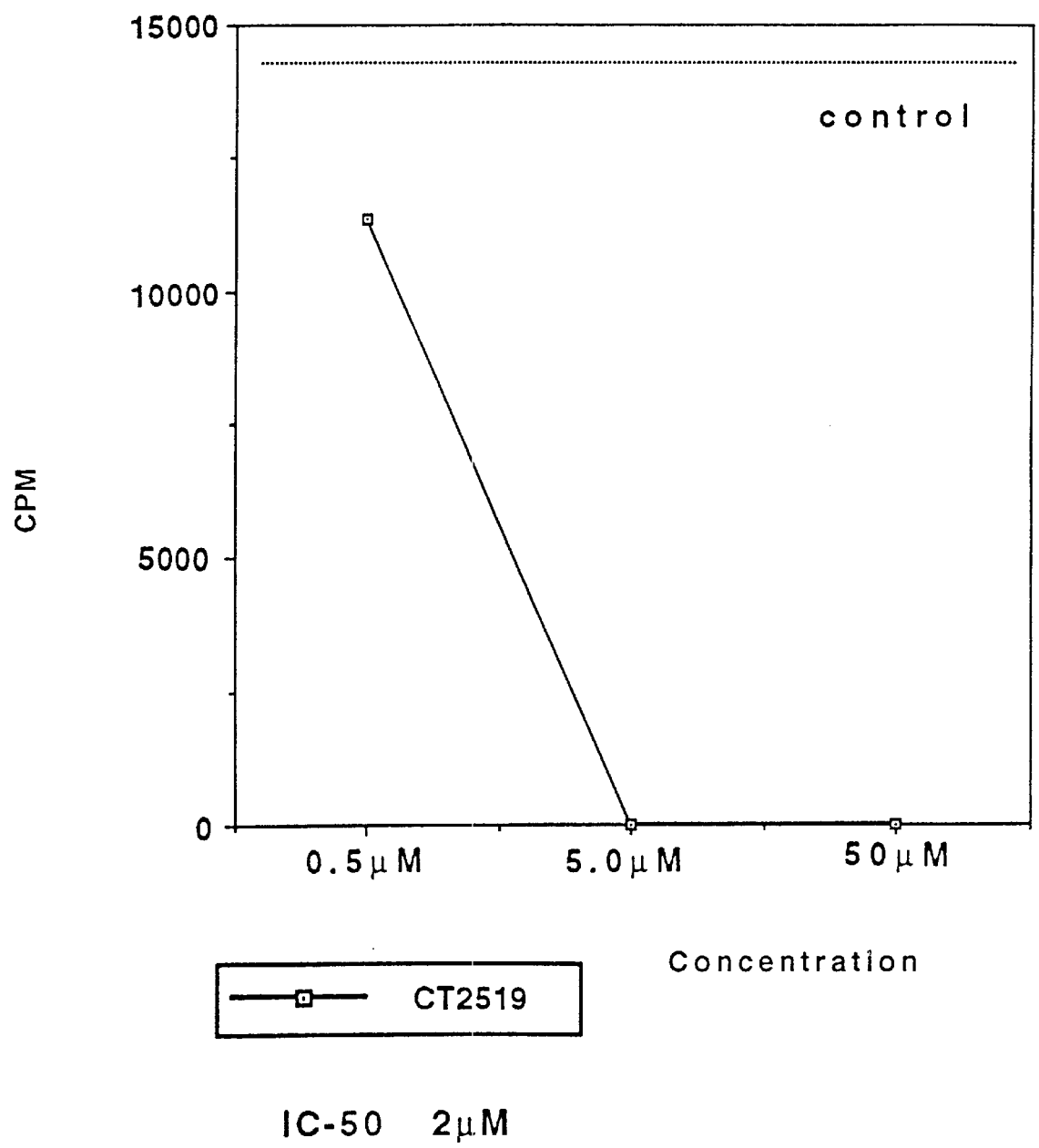
FIG. 3 shows a representative mixed lymphocyte reaction assay using inventive compound no. 2519 (see below for chemical names and structures).

FIG. 3 shows a representative mixed lymphocyte reaction assay of 2519 and illustrates a dose-response relationship for calculating $IC_{50}$ values. Inventive compound no. 2519 has significant dose-response activity in this immune modulating activity assay with an $IC_{50}$ of 2 µM.

EXAMPLE 16

Figure 4:
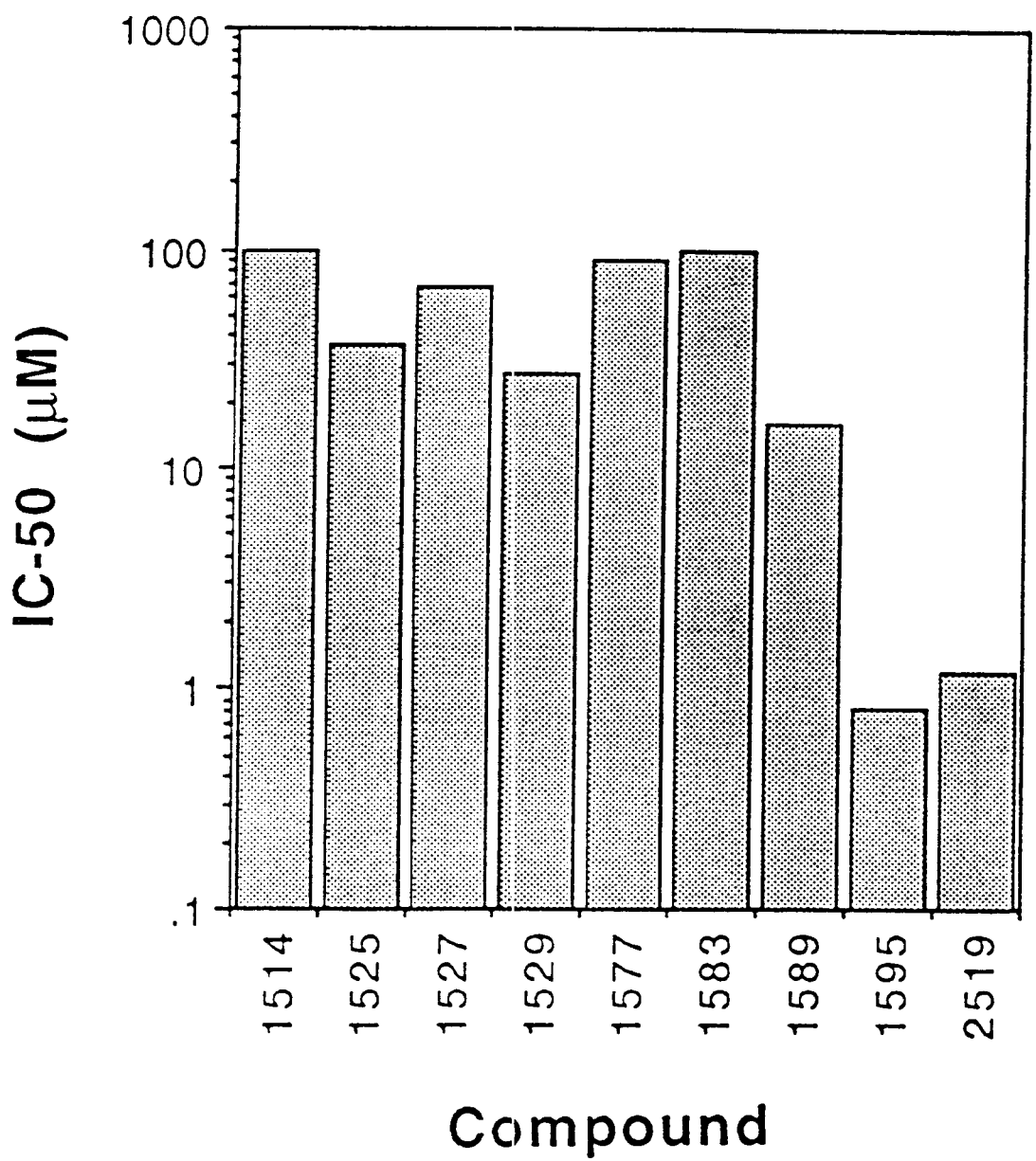
FIG. 4 illustrates effects of twelve representative inventive compounds on inhibition of murine thymocyte proliferation stimulated by concanavalin A (ConA) and interleukin-2 (IL-2).

This example illustrates the effect of 1514, 1525, 1527, 1529, 1577, 1583, 1589, 1595, and 2519 on inhibition of murine thymocyte proliferation stimulated by concanavalin A (ConA) and interleukin-2 (IL-2) (FIG. 4). Thymuses were obtained from normal, female Balb/C mice. The thymuses were dissociated and plated into 96-well plates at a density of 2×10$^5$ cells/well. ConA and IL-1α were added to the wells (ConA (0.25 mg/ml) and IL-1α (12.5 ng/ml)). The cells were incubated for 4 days at 37° C. On day 4, the cells were pulsed with tritiated thymidine and allowed to incubate for an additional 4 hrs. The cells were harvested and incorporated tritiated thymidine was determined in a liquid scintillation counter. Drug was added at the doses indicated two hours prior to activation with ConA and IL-1α. 1595 and 2519 were the most potent drugs in this immune suppression assay. Background counts were less than 200 cpm. This in vitro assay is a model for immune suppression and treatment or prevention of autoimmune diseases.

EXAMPLE 17

Figure 5:
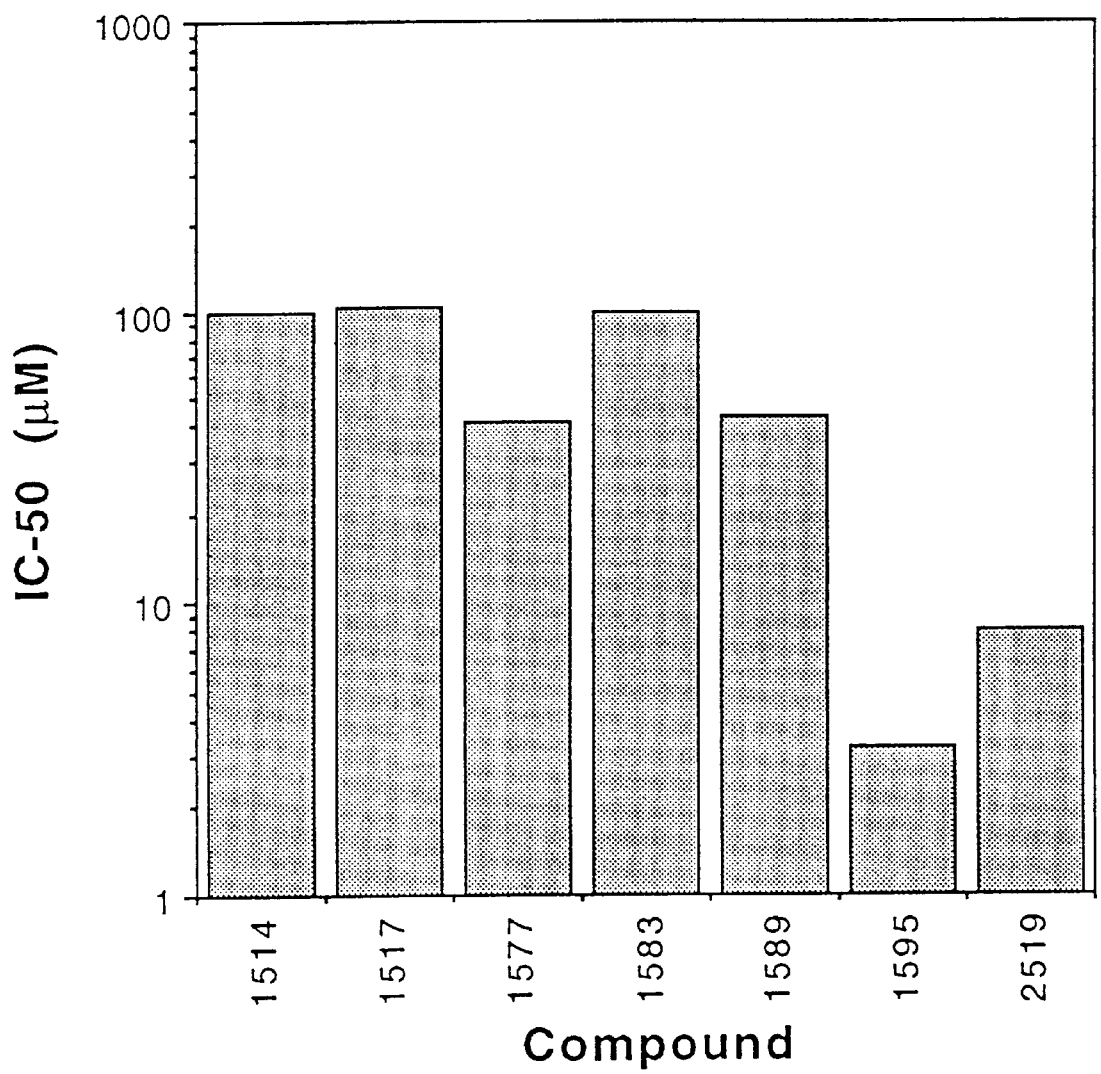
FIG. 5 shows the effects of seven inventive compounds on inhibition of murine splenocyte proliferation stimulated by anti-mu (10 mg/ml) and murine interleukin-4 (IL-4, 12.5 ng/ml).

This example illustrates the effects of 1514, 1517, 1577, 1583, 1589, 1595 and 2519 (see above for chemical names and structures) on inhibition of murine splenocyte proliferation stimulated by anti-mu (10 mg/ml) and interleukin-4 (IL-4, 12.5 ng/ml). This in vitro assay is described above and is an immune suppression and autoimmune treatment assay emphasizing a humoral or B cell immune response. Drug was added to the cells at the doses indicated two hours prior to activation with anti-mu and IL-4. This in vitro assay is a model for immune suppression and treatment or prevention of autoimmune diseases. As shown in FIG. 5, 2519 and 1595 were the most potent inhibitors of splenocyte proliferation in a dose-response manner. Background counts were less than 200 cpm.

EXAMPLE 18

Figure 6:
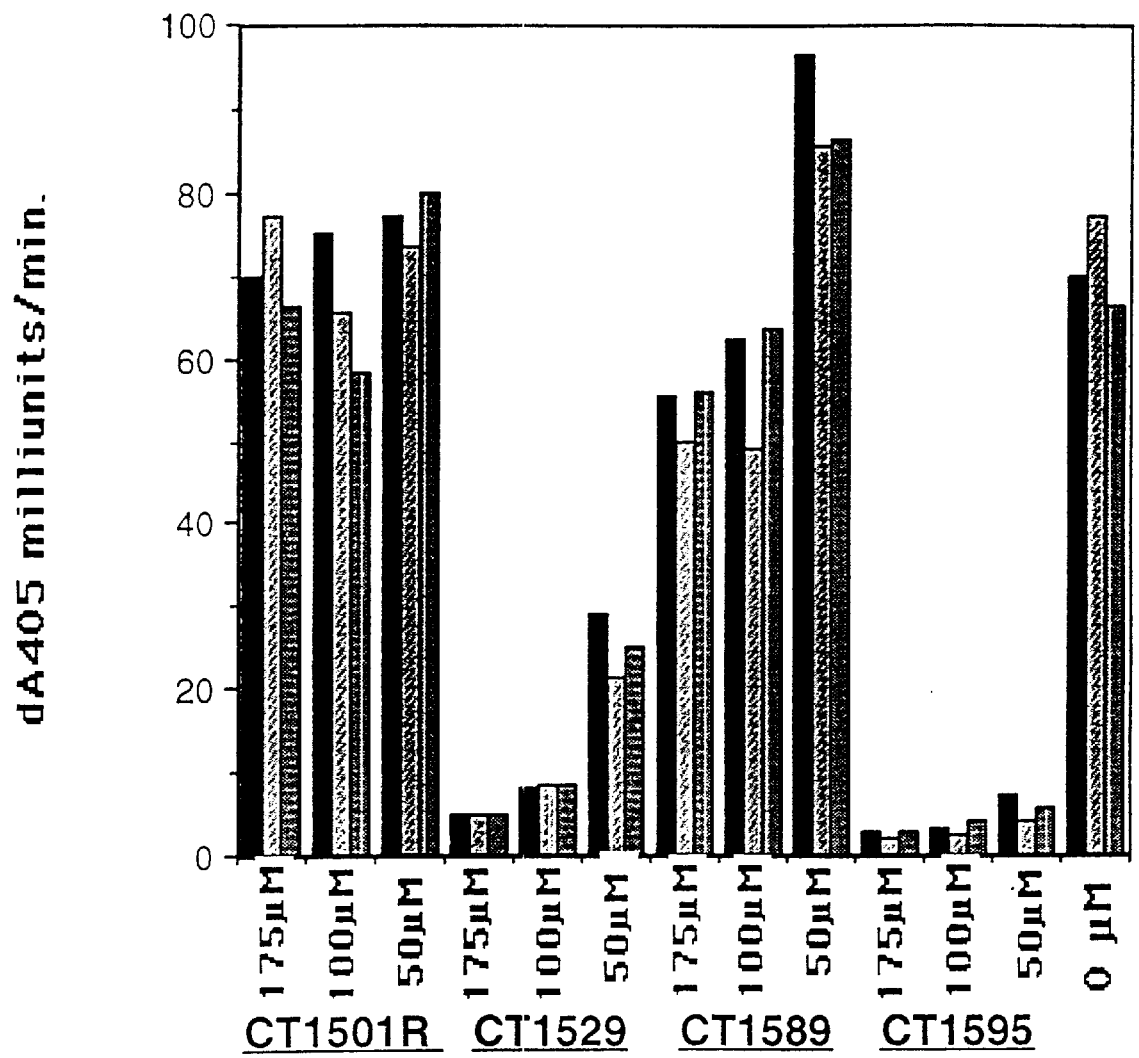
FIG. 6 shows the effects of a comparative compound and inventive compounds nos. 1529, 1589, and 1595 (see below for chemical names and structures) on yeast growth (*Saccharomyces cervisiae*).

This example illustrates the effects of comparative compound no. 1501R, R-1-(5-hydroxyhexyl)-3,7-dimethylxanthine, and inventive compounds nos. 1529, 1589 and 1595 (see above for chemical name and structure) on yeast growth (Saccharomyces cervisiae) in the presence or absence of drug. This assays measures anti-yeast and anti-fungal activity of the inventive compounds tested. Procedurally, a control yeast strain Saccharomyces cervisiae (BIO 101, Inc.) was grown overnight in YEPD broth at 30° C. A 1:100 dilution of the yeast culture was made with fresh YEPD broth. 100 $\mu$l Aliquots of the diluted culture were distributed into 96-wells titer plates. 100 $\mu$l Aliquots of inventive compound, diluted in YEPD broth, were then added to the wells. The titer plates were incubated at room temperature with continuous shaking. The cell density of the individual cultures was determined using a microplate reader with a A630 filter. The A630 of the individual yeast cultures were compared to control samples prepared in the absence of inventive compound. As shown in FIG. 6, inventive compound no. 1595 strongly inhibited yeast growth and is a potential topical or systemic antimicrobial therapy, as predicted by data obtained in this in vitro model.

EXAMPLE 19

Figure 7:
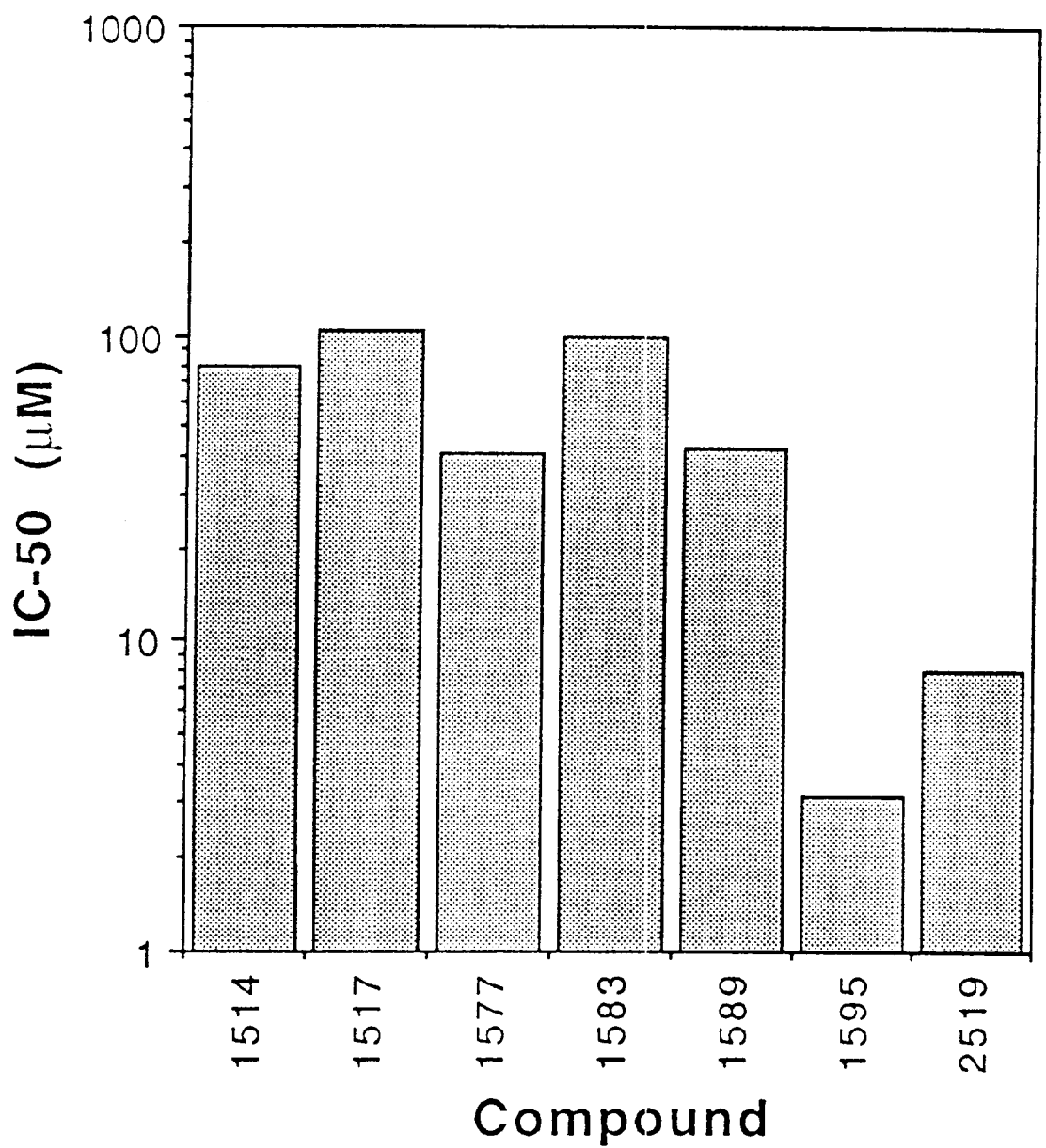
FIG. 7 illustrates an ability of seven inventive compounds (see below for chemical name and structure) to strongly inhibit proliferation of human stromal cells stimulated with PDGF and IL- 1.

This example illustrates the effects of 1514, 1517, 1577, 1583, 1589, 1595 and 2519 (see above for chemical name and structure) to strongly inhibit proliferation of human stromal cells when stimulated with PDGF. This assay is a model for restenosis and treatment of atherosclerosis and coronary artery disease. Stromal cells were starved in serum-free media for one day and then stimulated with 50 ng/ml PDGF-BB. The drugs were added at the indicated concentrations one hour prior to PDGF stimulation. Tritiated thymidine was added for one day at the time of PDGF stimulation and the cells were harvested and counted by liquid scintillation counting 24 hours later. Background counts (i.e., starved cells) were approximately 1% of control levels. FIG. 7 shows that all inventive compounds were active in this predictive in vitro model with inventive compounds nos. 1595 and 2519 exhibiting the most potent activity.

EXAMPLE 20

Figure 8:
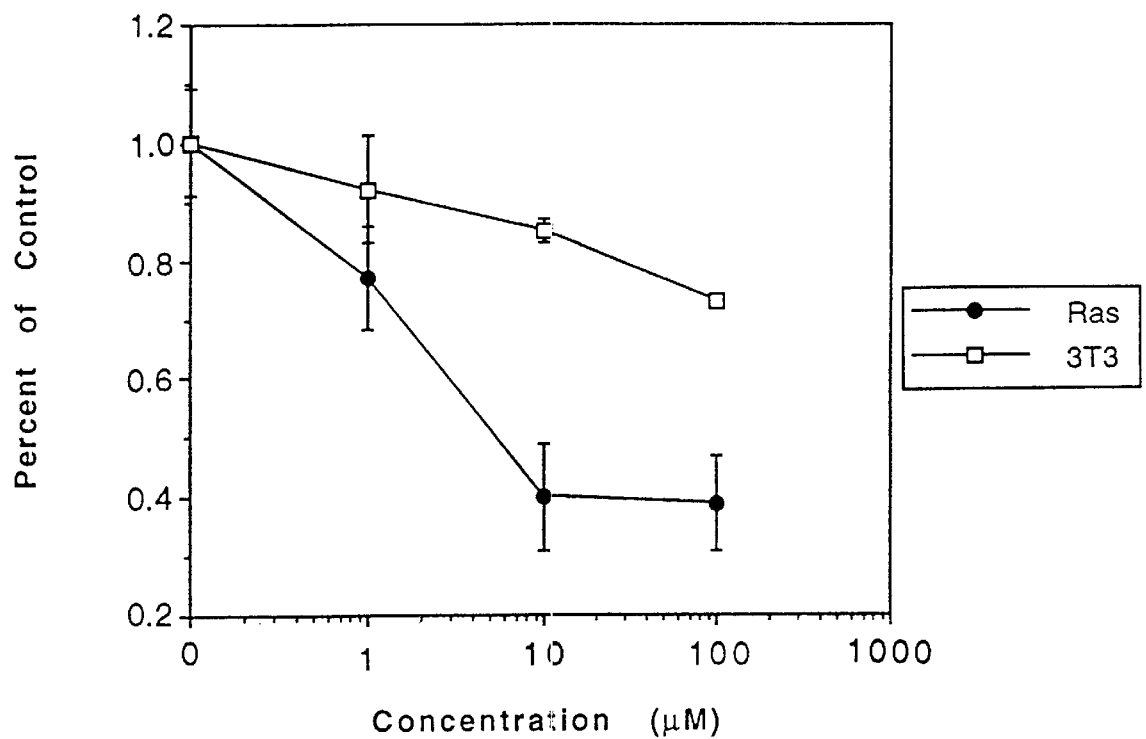
FIG. 8 shows a comparison of cytotoxicity determinations for inventive compound no. 1595 in transformed cells (Ras 3T3) and in normal 3T3 cells.
Figure 9:
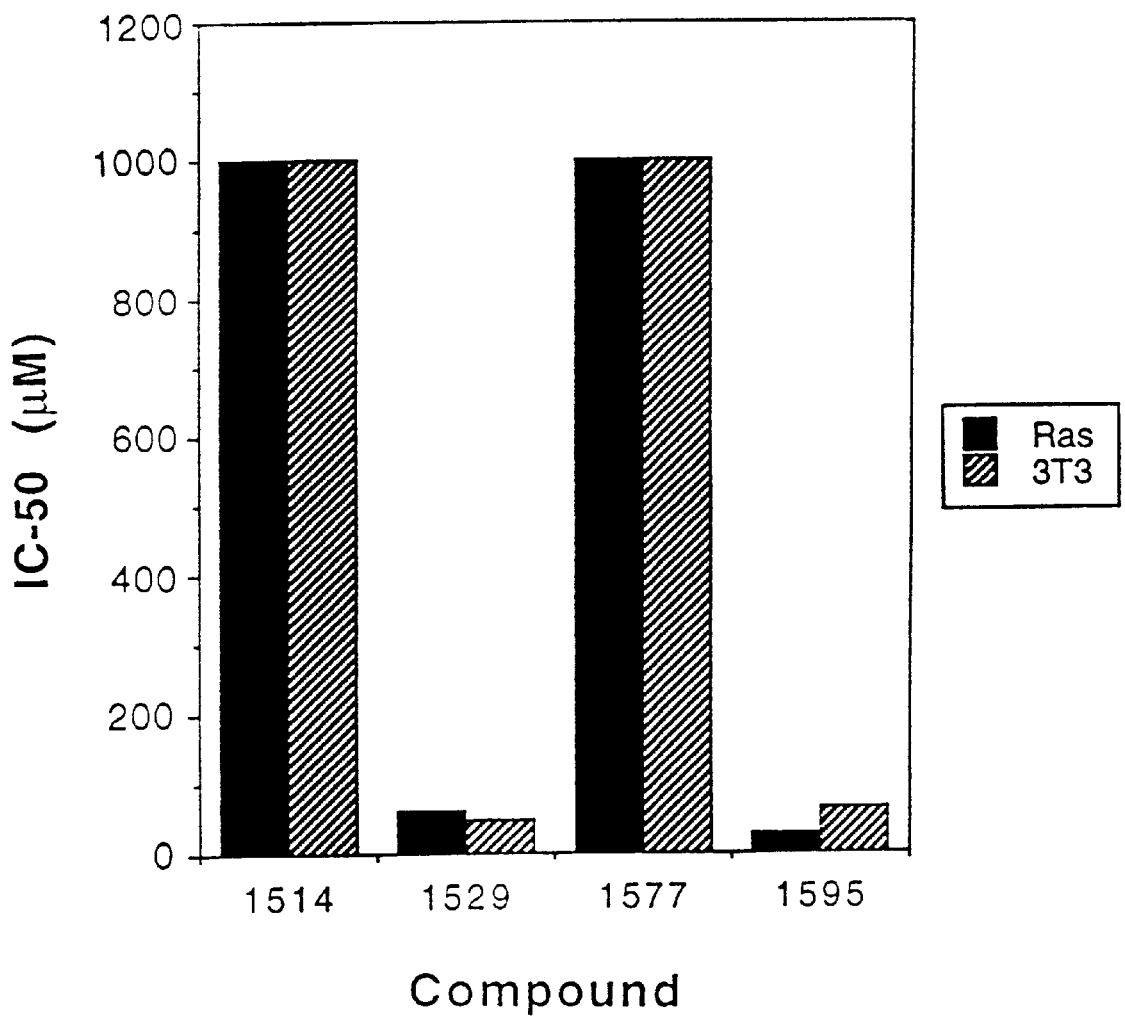
FIG. 9 illustrates results for five inventive compounds in an assay protocol similar to that used to obtain results reported in FIG. 8 above.

This example illustrates a comparison of cytotoxicity determinations for inventive compound no. 1595 in transformed cells (Ras 3T3) and in normal 3T3 cells at drug doses of 1, 10 and 100 $\mu$M using in vitro cell culture conditions (FIG. 8). At each concentration tested, compound no. 1595 was more cytotoxic for the cancer cell than the normal cell, indicating differential toxicity for tumor cells and potential usefulness as a cancer chemotherapeutic agent. A similar experiment is shown in FIG. 9 for five inventive compounds (see above for chemical names and structure) showing differential cytotoxicity for the same normal and transformed cells. Only inventive compounds nos. 1529 and 1595 showed significant cytotoxic activity in this in vitro model for cancer chemotherapeutic agent applications.

EXAMPLE 21

Figure 10:
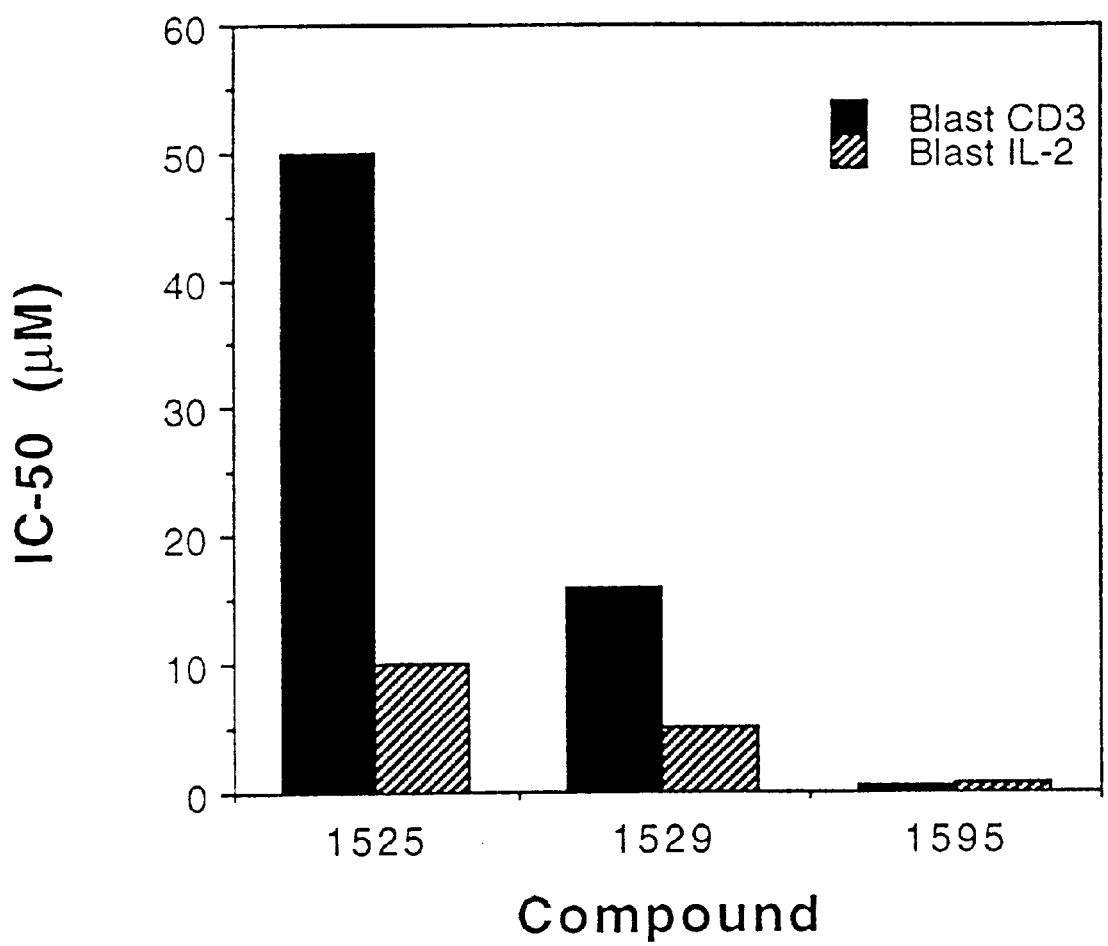
FIG. 10 shows the effects of three inventive compounds on inhibition of blast formation from human lymphocytes stimulated by IL-2 or an anti-CD3 antibody.

This example illustrates an experiment showing the effects of 1525, 1529 and 1595 (see above for chemical names and structures) on inhibition of blast formation from human lymphocytes stimulated by IL-2 or an anti-CD3 antibody (FIG. 10). This is a human in vitro assay for immunosuppressive activity of the inventive compounds. Of the three compounds tested, 1595 demonstrated significant immunosuppressive activity of blastogenesis stimulated by either IL-2 or anti-CD3 with $IC_{50}$ values below 5 $\mu$M.

EXAMPLE 22

This example illustrates the effects of inventive compound no. 1595 on the amount of DAG (diacylglycerol--FIG. 11) and PA (phosphatidic acid--FIG. 12), generated at different times after stimulation of Ras-transformed 3T3 cells with IL-1$\beta$. Procedurally, target cells were incubated with a primary stimulus (e.g., in this case, Ras-transformed 3T3 cells were incubated with IL-1$\beta$). After incubation for a short period, cell lipids were extracted and assayed by thin layer chromatography according to standard procedures.

Lipids were extracted using, for example, chloroform-:methanol 2:1 (v/v), and the extracts were then subjected to HPLC as described in Bursten and Harris, *Biochemistry*, vol. 30, 6195–6203 (1991). A Rainin® mu-Porasil column was used with a 3:4 hexane:propanol organic carrier and a 1–10% water gradient during the first 10 minutes of separation. Detection of the peaks in the elution pattern was by absorption in the range of ultraviolet which detects isolated double bonds. The relevant peaks of unsaturated PA and DAG were shown in the elution pattern. It is important to note that the assay method permits discrimination between various forms of PA and DAG so that those relevant to the pathway affected by the inventive compounds were measured directly. Confirmation of the nature of the acyl substituents of these components was accomplished using fast-atom bombardment mass spectroscopy. Thus, the relevant PA and DAG subspecies may be detected. The time periods employed were 5–60 seconds after stimulation with IL-1$\beta$.

Figure 11:
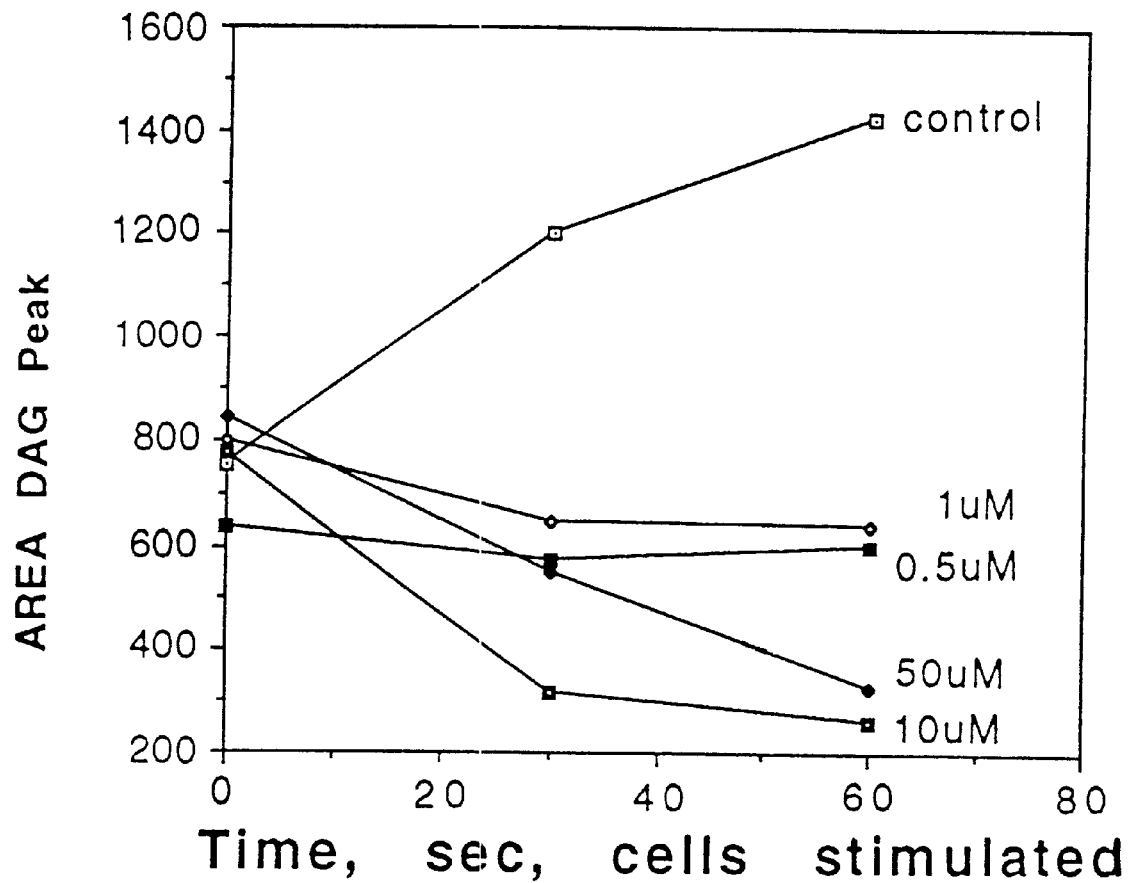
FIGS. 11 and 12 show the effects of inventive compound no. 1595 on the amount of DAG (diacylglycerol—FIG. 1) and PA (phosphatidic acid—FIG. 12) generated at different times after stimulation of Ras-transformed 3T3 cells with IL-1β.
Figure 12:
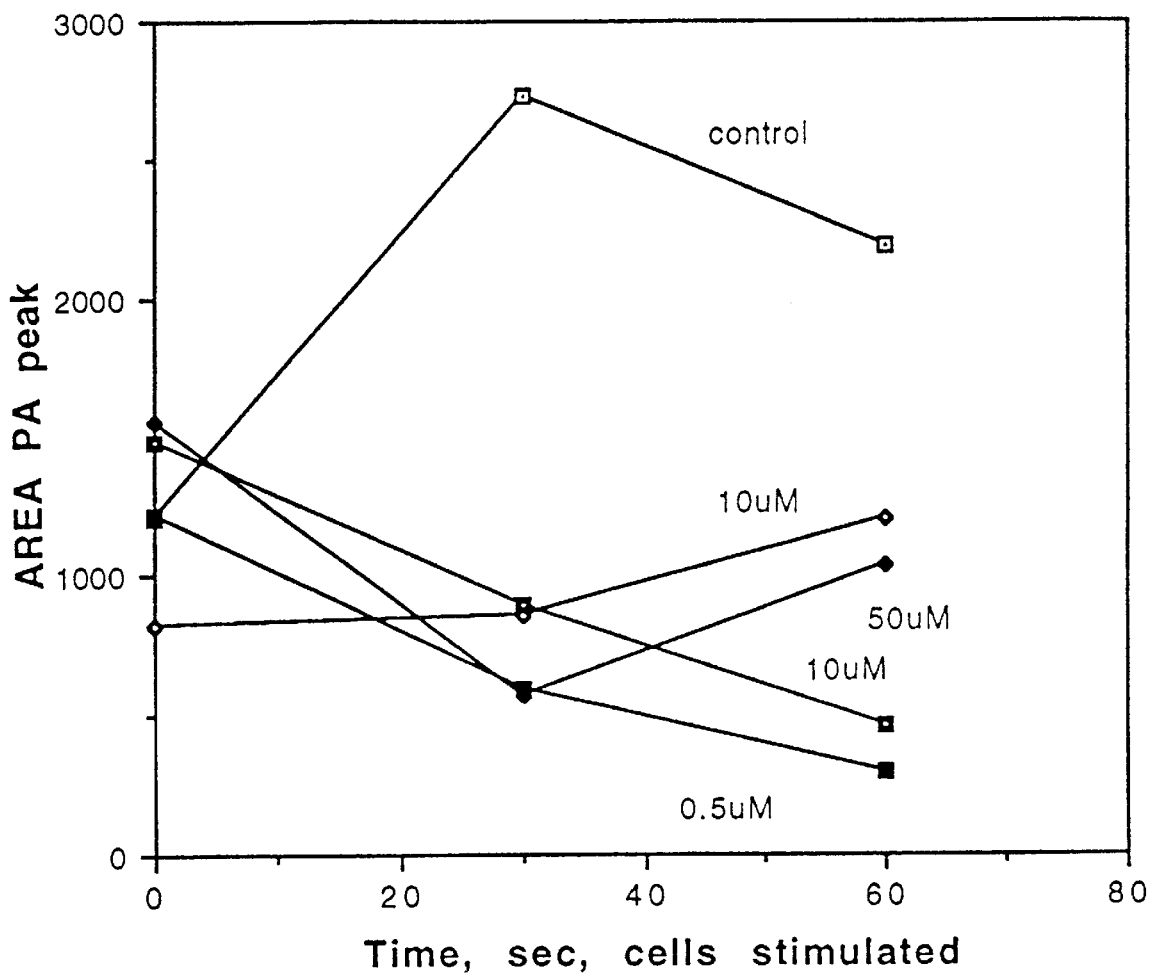

In the results illustrated in FIGS. 11 and 12, inventive compound no. 1595 was a potent inhibitor of enzyme activity generating PA and DAG by inhibiting IL-1$\beta$-induced signal transduction through this second messenger pathway. The inhibiting activity was not in a dose-response manner, indicating that the $IC_{50}$ concentration for inhibiting cellular second messenger signaling is probably below 500 nM. It is not evident which enzyme or enzymes were inhibited by compound no. 1595. However, the overall signal is being significantly inhibited, as corroborated by the effects of this compounds in vitro on other predictive, disease models.

Figure 13:
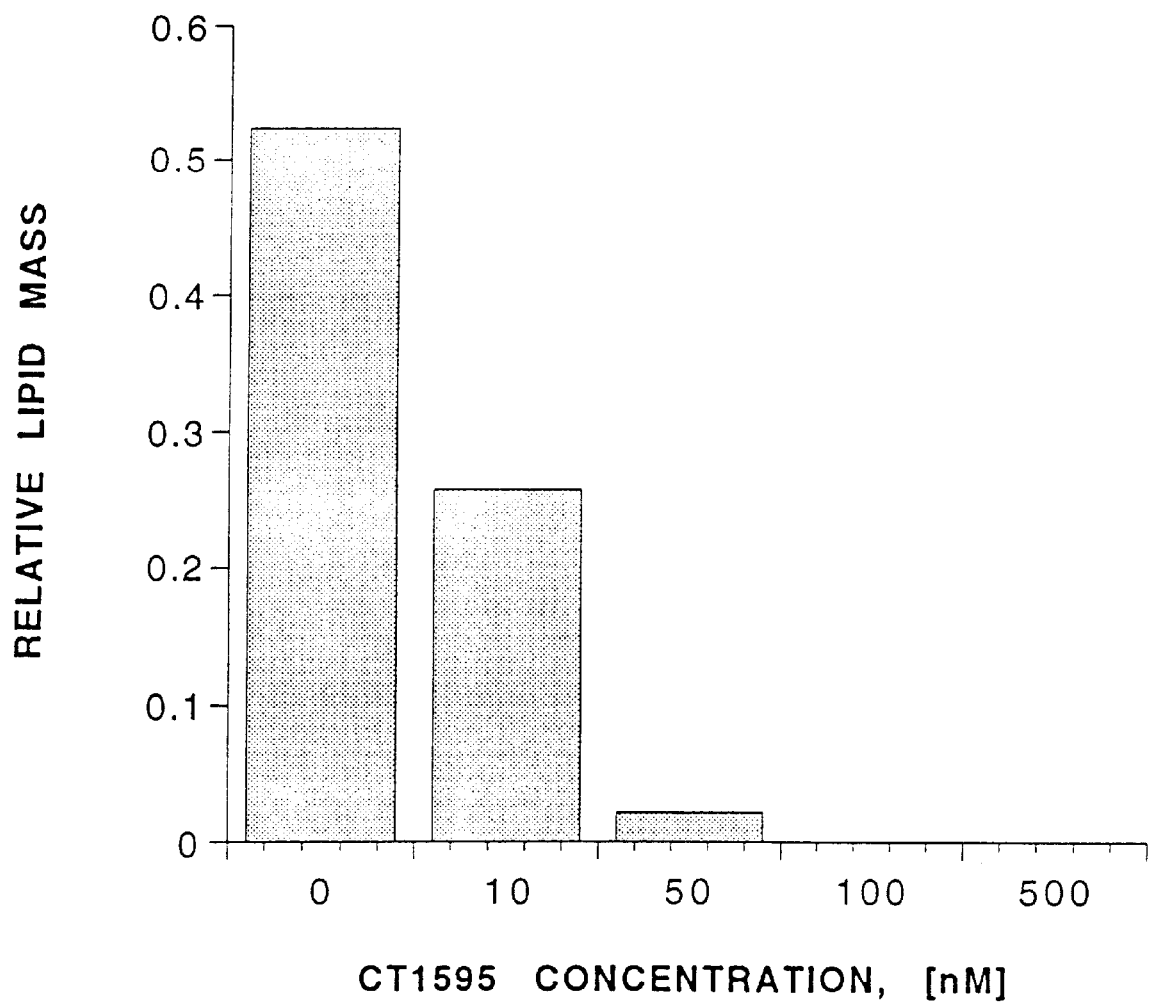
FIG. 13 reports data showing the effect of different nanomolar concentrations of inventive compound no. 1595 on the total phosphatidic acid mass in a mast cell line (PT-18) stimulated by administration of IgE and dinitrophenol (DNP).

FIG. 13 shows the effect of different nanomolar concentrations of inventive compound no. 1595 on total PA mass in a mast cell line (PT-18) stimulated by administration of IgE and dinitrophenol (DNP). These data show that the $IC_{50}$ of 1595 is in the low nanomolar range for accumulation of PA.

EXAMPLE 23

This example illustrates a comparative experiment comparing inventive compounds nos. 1595, 1529 and 2519 in an ex vivo human TNF model described herein. This assay is a predictive model for treatment and prevention of septic shock and sepsis syndrome and examines whether LPS-mediated release of TNF from monocytes in whole blood can be blocked by an inventive compound. In this assay, LPS was added to whole blood (normal human volunteers) to trigger a dose-dependent synthesis and extracellular release of TNF according to Desch et al., *Lymphokine Res.*, vol. 8, 141 (1989).

Procedurally, whole blood was collected from a healthy human donor into vacutainer tubes containing ACD citrate as anti-coagulant. The compounds tested were diluted in RPMI medium and 5 μl of the dilute concentrations placed in tubes containing 225 μl of whole blood. The tubes were mixed and incubated for no more than 1 hour at 37° C. LPS Salmonella abortus equi (commercially available from Sigma) is diluted in RPMI and the dilute samples added to the whole blood/compound samples at 20 μl per tube (10 ng/ml final concentration). The tubes are again mixed and incubated for an additional 4–6 hours at 37° C. Activity is stopped by adding 750 μl of RPMI to each tube, centrifuging and removing the cells. Supernatants are collected and stored overnight at 4° C. The supernatant samples are assayed for TNF release using immunoassay kits (available commercially from Biosource International, Camarillo, Calif.).

Figure 14:
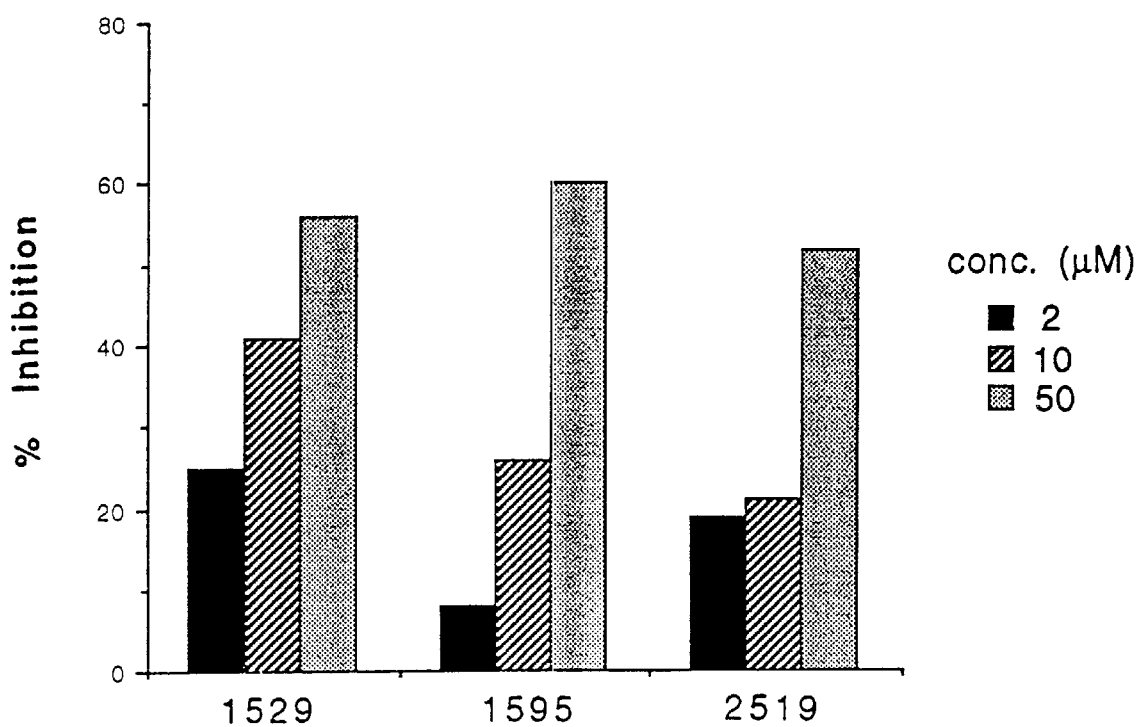
FIG. 14 shows a comparison of inventive compounds nos. 1595, 1529 and 2519 in an ex vivo human TNF model, which is a predictive model for treatment and prevention of septic shock and sepsis syndrome.

All three inventive compounds tested blocked TNF release in a dose-dependent fashion, as shown in FIG. 14. However, inventive compound no. 1529 was the most effective agent at lower doses, doses more likely achievable in vivo.

EXAMPLE 24

Figure 15:
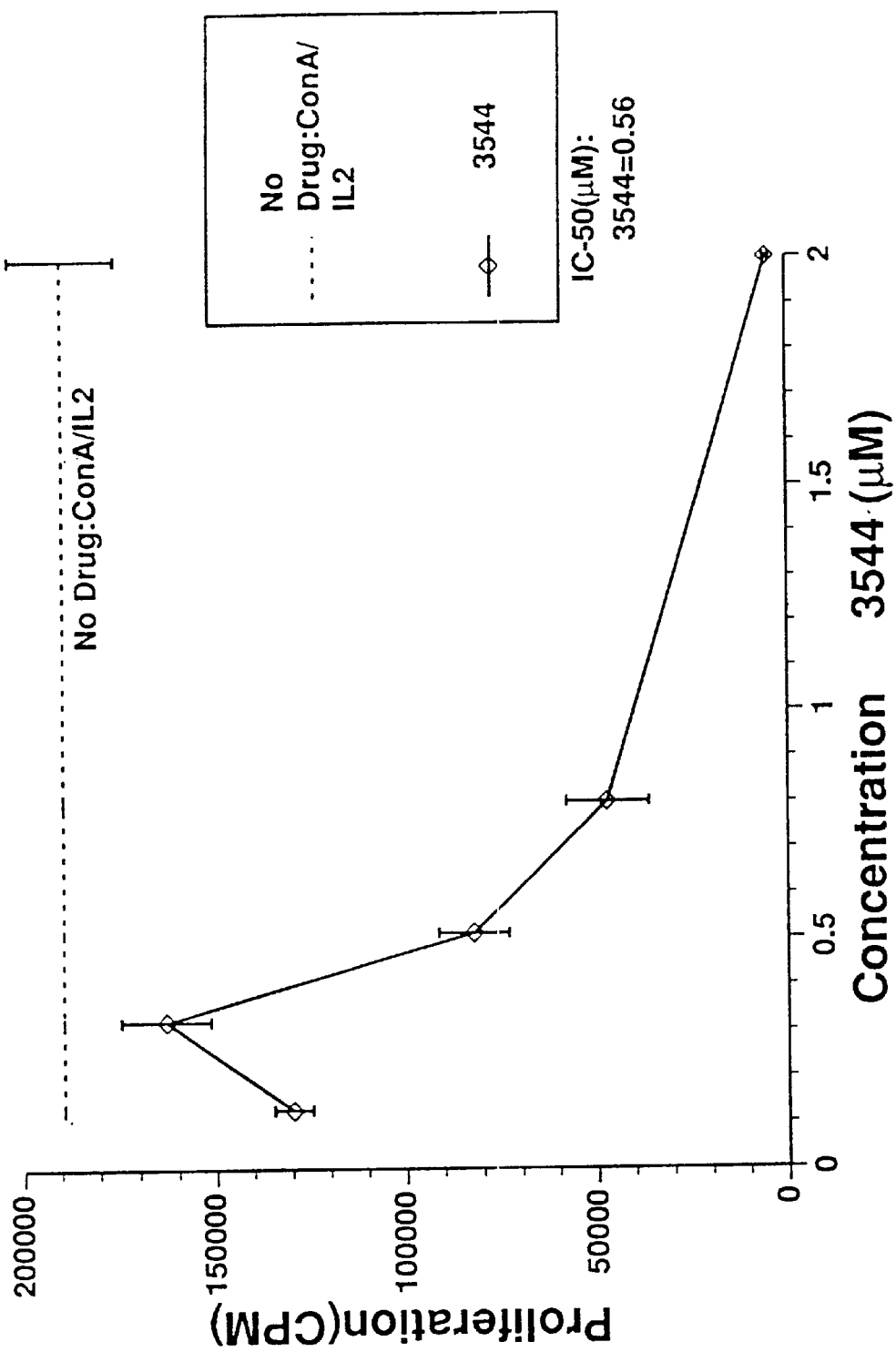
FIGS. 15 and 16 report data obtained in a thymocyte proliferation assay, measuring an ability of inventive compounds nos. 3544 and 3567 to inhibit proliferation co-stimulated by ConA and IL-2.
Figure 16:
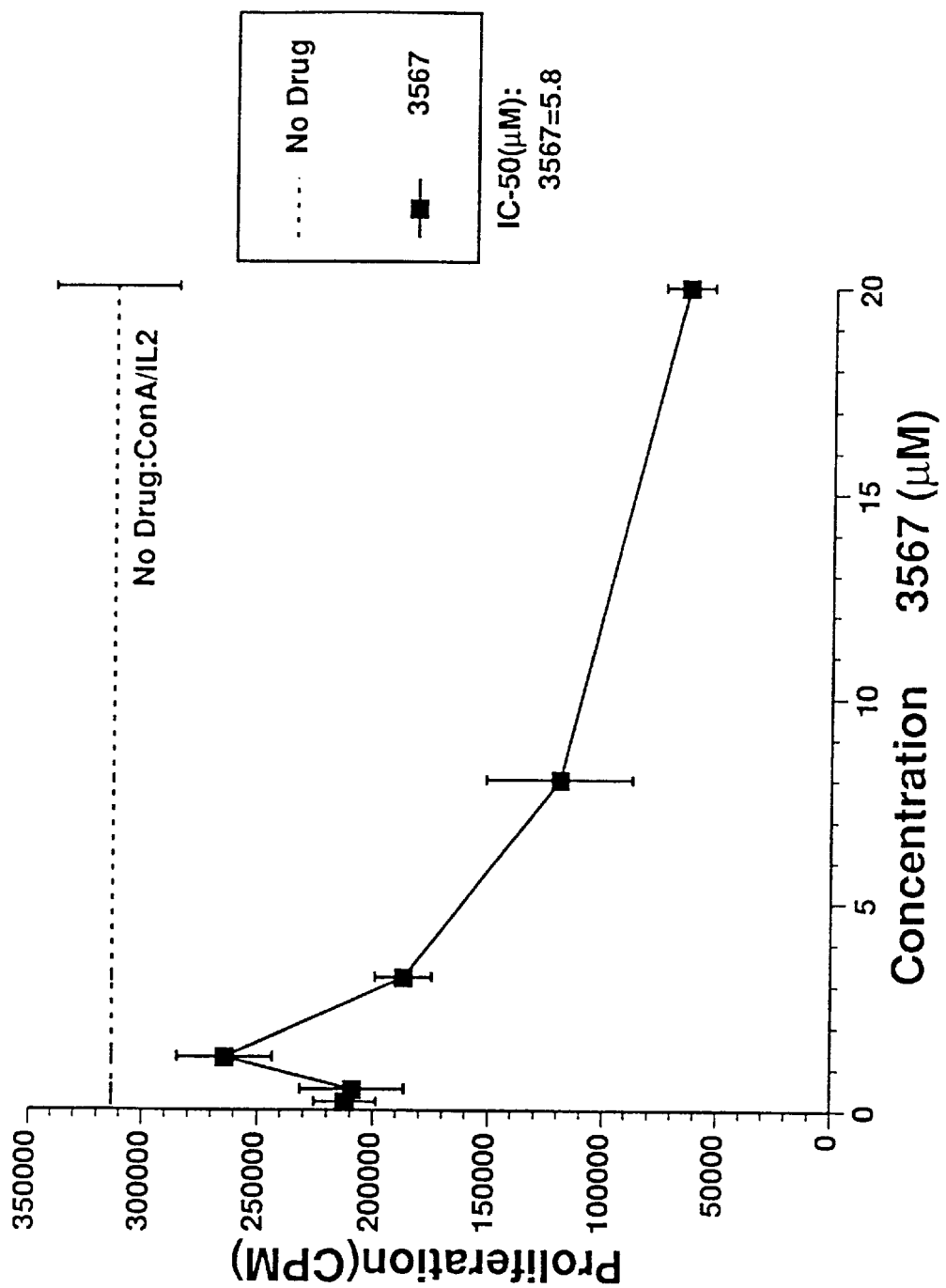

This example illustrates the inhibitive effect of two additional compound of the invention in an assay protocol used in Example 18, the thymocyte proliferation assay. As shown by the data presented in FIGS. 15 and 16, these compounds inhibited proliferation of thymocytes co-stimulated by ConA and IL-2 in a dose-response manner. Experimentally calculated $IC_{50}$ values for the two representative compounds nos. 3544 and 3567 are 0.56 and 5.8, respectively.

What is claimed is:

1. A compound, including resolved enantiomers and/or diastereomers, hydrates, salts, or solvates, having the formula:

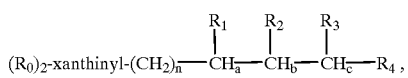

I wherein $R_0$ is selected from the group consisting of hydrogen, halo, hydroxyl, amino, substituted or unsubstituted $C_{(1-10)}$ alkyl, $C_{(2-10)}$ alkenyl, cyclic or heterocyclic groups, wherein the substituents of substituted $C_{(1-10)}$ alkyl, $C_{(2-10)}$ alkenyl are other than halo;

n is an integer from one to sixteen;

$R_1$, $R_2$, and $R_3$ are independently selected from the group consisting of a halo; haloacetoxy; hydrogen; hydroxy; oxo; —N=C=S; —N=C=O; —O—C≡N; —C≡N; —N=N=N; and —C—$(R_5)_3$, $R_5$ being independently a halo or hydrogen, at least one $R_5$ being halo, at least one of $R_1$, $R_2$, and $R_3$ being halo, cyano, isocyano, isothiocyano, azide or haloacetoxy group;

$R_4$ is hydrogen, $C_{(1-6)}$ alkyl, $C_{(1-6)}$ alkenyl, cyclo $C_{(4-6)}$ alkyl, or phenyl;

one or more hydrogen atoms of $(CH_2)_n$—$CH_a$—$CH_b$—$CH_c$ may be replaced with: i) halo, hydroxyl, oxo, and substituted or unsubstituted $C_{(1-10)}$ alkyl, $C_{(1-10)}$ alkoxyalkyl, $C_{(2-10)}$ alkenyl, cyclic, or heterocyclic group; or ii) one or two unsaturated bonds; and any two adjacent carbon atoms of $(CH_2)_n$—$CH_a$—$CH_b$—$CH_c$ may be separated by at least one oxygen atom.

2. The compound of claim 1, wherein $R_2$ and $R_3$ are selected from the group consisting of halo, oxo, and hydroxyl group.

3. The compound according to claim 1, wherein one of $R_1$, $R_2$, and $R_3$ is chloro, bromo, or fluoro.

4. The compound according to claim 1, wherein both of $R_0$ are methyl.

5. The compound according to claim 1, wherein one or two $R_0$ are selected from the group consisting of, cyclohexyl, cyclopentyl, 3-dimethylaminobutyl, ethyl, hexyl, 2-hydroxyethyl, 5-hydroxyhexyl, 3-hydroxy-n-butyl, 3-hydroxypropyl, isobutyl, isopropyl, 2-methoxyethyl, 4-methoxy-n-butyl, methyl, n-butyl, n-propyl, phenyl and t-butyl.

6. The compound according to claim 1, wherein one or more hydrogen atoms of $(CH_2)_n$—$CH_a$—$CH_b$—$CH_c$ is replaced with i) halo, hydroxyl, oxo, or substituted or unsubstituted $C_{(1-10)}$ alkyl, $C_{(1-10)}$ alkoxyalkyl, $C_{(2-10)}$ alkenyl, cyclic, or heterocyclic group; or ii) one or two unsaturated bonds; or wherein any two adjacent carbon atoms of $(CH_2)_n$—$CH_a$—$CH_b$—$CH_c$ are separated by at least one oxygen atom.

7. The compound according to claim 6, wherein corresponding substituents are selected from the group consisting of carbamoyl, primary, secondary and tertiary amino, $C_{(2-8)}$ alkenyl, $C_{(1-8)}$ alkyl, $C_{(1-8)}$ alkoxy, $C_{(1-8)}$ hydroxyalkyl, azidyl, oxo, carboxyl, cyano, $C_{(1-8)}$ haloalkyl, isocyano, isothiocyano, phosphate, phosphonate, sulfonate, sulfone, sulfoxyl, thioamido, thiocarbonyl, thioester, thiol, thiourea and urea.

8. The compound according to claim 1, wherein any two adjacent carbon atoms of $(CH_2)_n$—$CH_a$—$CH_b$—$CH_c$ are separated by at least one oxygen atom.

9. The compound according to claim 1, wherein each of the cyclic or heterocyclic groups is selected from the group consisting of anthracene, bicyclo[4.4.0]decane, bicyclo [2.2.1]heptane, bicyclo[3.2.0]heptane, bicyclo[4.1.0] heptane, bicylo[2.2.1]hexane, bicyclo[4.3.0]nonane, bicyclo [2.2.2]octane, biphenyl, cyclopentadiene, cyclopentane, cyclobutane, cyclobutene, cycloheptane, cyclohexane, cyclooctane and cyclopropane, 1,2-diphenylethane, fluorene, indene, phenyl, quinone, terphenyl, napthalene, phenanthrene, terphenyl, toluene, xylene, azetidine, benzofuran, benzothiophene, carbazole, furan, glutarimide, indole, isoquinoline, lactam, lactone, oxazole, oxetane, oxirane, phthalimide, piperidine, pyrrolidine, pyran, pyridine, pyrrole, quinoline, tetrahydrofuran, tetrahydropyran, tetrahydrothiophene, thiophene, thymine and derivatives thereof.

10. The compound according to claim 1, wherein the compound is selected from the group consisting of:

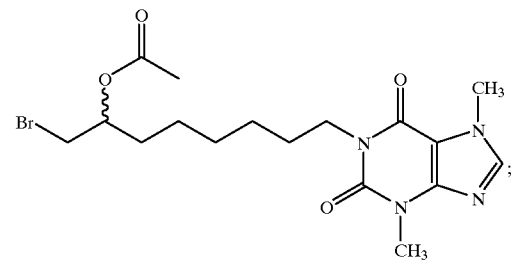

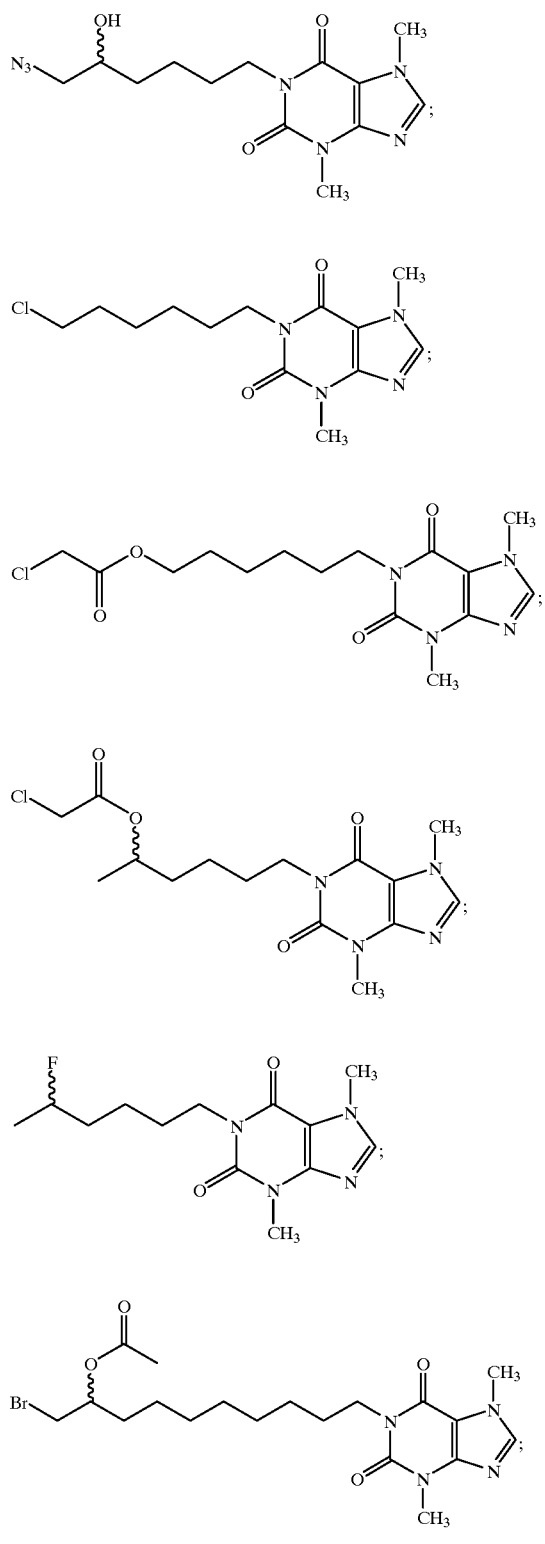
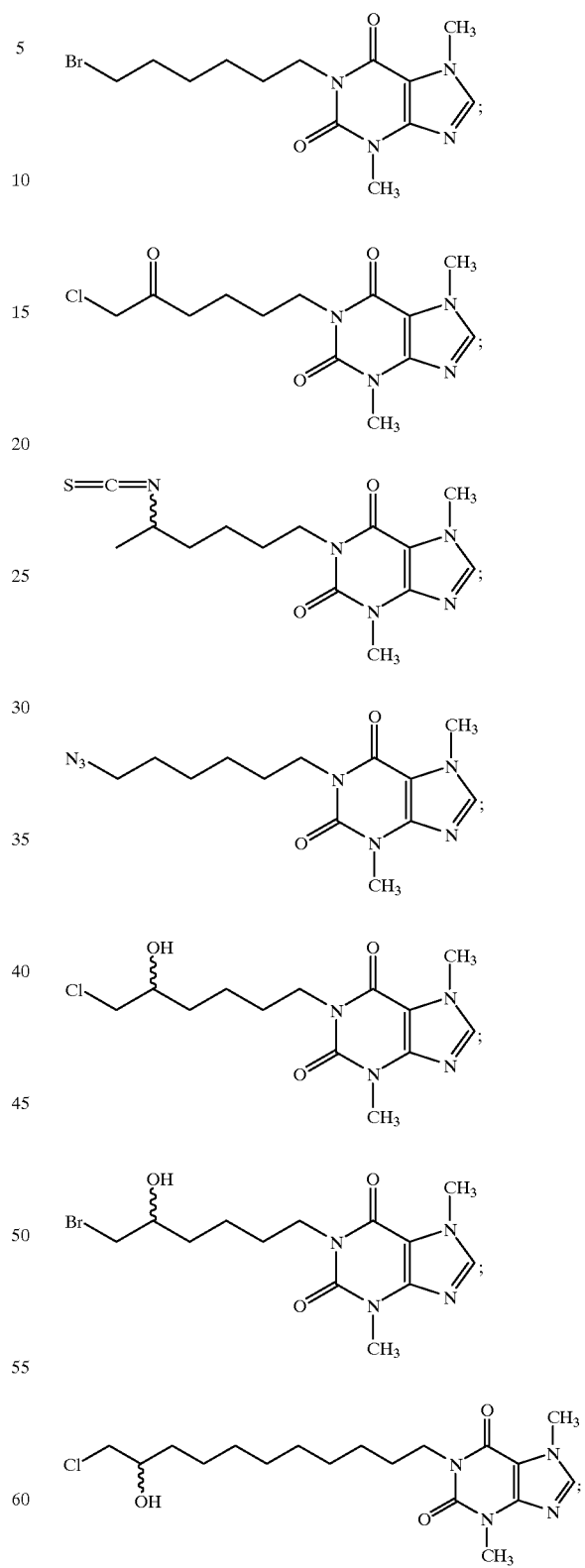

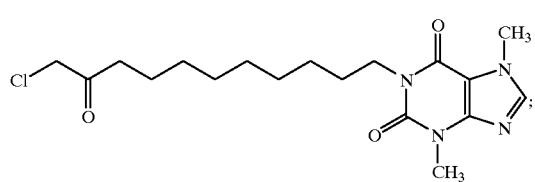

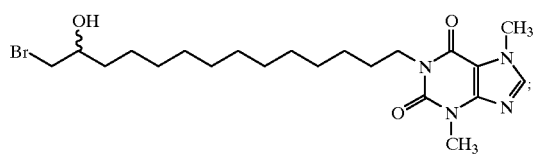

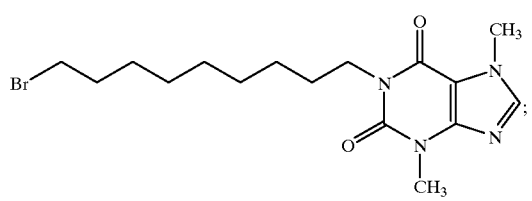

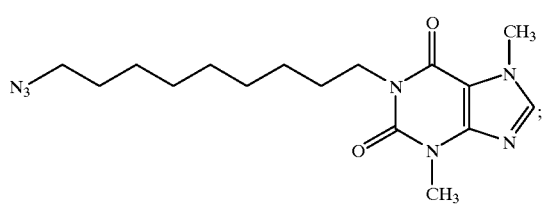

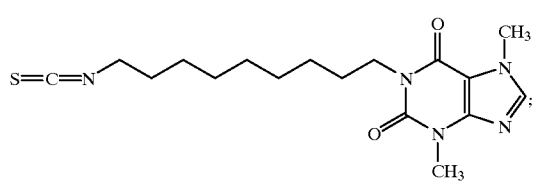

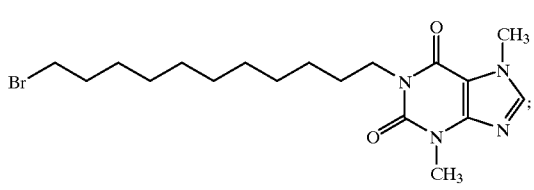

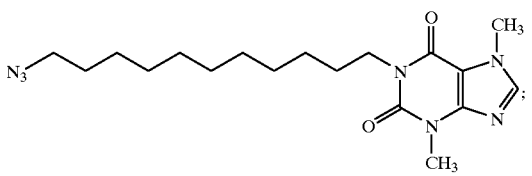

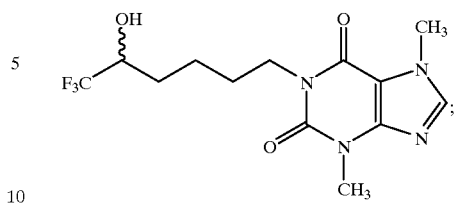

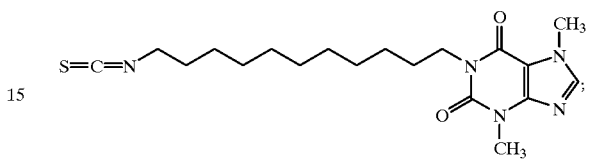

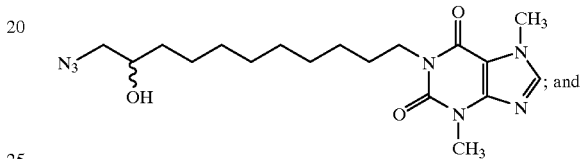

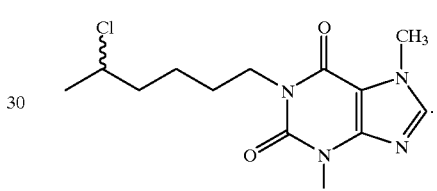

11. A pharmaceutical composition comprising a compound according to claim 1 and a suitable carrier, diluent or excipient.

12. The pharmaceutical composition of claim 11, wherein the composition is formulated for parenteral, topical or oral administration or for inhalation.

13. The pharmaceutical composition of claim 11 wherein the dose of compound is from about 50 mg to about 5000 mg per day.

14. The pharmaceutical composition of claim 11 wherein the parenteral dose of compound is from about 0.001 mg/kg to about 40 mg/kg per day.

15. The pharmaceutical composition of claim 11 wherein the parenteral dose of compound is from about 0.01 mg/kg to about 20 mg/kg per day.

16. The pharmaceutical composition of claim 11 wherein the oral dose of compound is from about 0.1 mg/kg to about 1000 mg/kg per day.

17. The pharmaceutical composition of claim 11 wherein the intranasal dose of compound is from about 0.001 mg/kg to about 40 mg/kg per day.

* * * * *